(12) United States Patent
Jones et al.

(10) Patent No.: US 11,592,448 B2
(45) Date of Patent: Feb. 28, 2023

(54) TANDEM IDENTIFICATION ENGINE

(71) Applicant: DiscernDx, Inc., Palo Alto, CA (US)

(72) Inventors: Jeffrey Jones, Glendale, CA (US);
William Smith, San Marcos, CA (US)

(73) Assignee: DiscernDx, Inc., Palo Alto, CA (US)

(*) Notice: Subject to any disclaimer, the term of this patent is extended or adjusted under 35 U.S.C. 154(b) by 442 days.

(21) Appl. No.: 16/622,746

(22) PCT Filed: Jun. 13, 2018

(86) PCT No.: PCT/US2018/037417
§ 371 (c)(1),
(2) Date: Dec. 13, 2019

(87) PCT Pub. No.: WO2018/232043
PCT Pub. Date: Dec. 20, 2018

(65) Prior Publication Data
US 2020/0110096 A1    Apr. 9, 2020

Related U.S. Application Data

(60) Provisional application No. 62/519,294, filed on Jun. 14, 2017.

(51) Int. Cl.
*G01N 33/68* (2006.01)
*G16B 35/20* (2019.01)
*H01J 49/00* (2006.01)

(52) U.S. Cl.
CPC ......... *G01N 33/6848* (2013.01); *G16B 35/20* (2019.02); *H01J 49/0036* (2013.01); *H01J 49/004* (2013.01)

(58) Field of Classification Search
CPC . G01N 33/6848; G16B 35/20; H01J 49/0036; H01J 49/004
See application file for complete search history.

(56) References Cited

U.S. PATENT DOCUMENTS 6,539,102 B1*  3/2003  Anderson ............ G16B 50/30
                                           382/128
2005/0048564 A1*  3/2005  Emili .................... G16B 30/00
                                           435/7.1

(Continued)

FOREIGN PATENT DOCUMENTS

WO   WO-2008142579 A2   11/2008
WO   WO-2017173390 A1   10/2017

(Continued)

OTHER PUBLICATIONS

Gallien, S. et al., Large-scale targeted proteomics using internal standard triggered-parallel reaction monitoring (IS-PRM), Molecular & Cellular Proteomics, 2015, vol. 14, pp. 1630-1644.

(Continued)

*Primary Examiner* — David A Vanore
(74) *Attorney, Agent, or Firm* — Wilson Sonsini Goodrich & Rosati

(57) ABSTRACT

Methods and computer systems related to image-based data analysis such as mass spectrometric data analysis. Methods and computer systems herein utilize multiple micro-processes operating concurrently to carry out rapid, efficient, and automated analysis of mass spectrometry data.

20 Claims, 5 Drawing Sheets

(56) References Cited

U.S. PATENT DOCUMENTS

| | | |
|---|---|---|
| 2006/0004525 A1 | 1/2006 | Washburn et al. |
| 2006/0172429 A1* | 8/2006 | Nilsson .............. G01N 33/6851 |
| | | 436/71 |
| 2007/0023630 A1 | 2/2007 | Malek et al. |
| 2013/0080073 A1 | 3/2013 | De Corral |
| 2019/0113520 A1* | 4/2019 | Blume .................. G16H 50/30 |
| 2020/0110096 A1* | 4/2020 | Jones ................. H01J 49/0036 |
| 2020/0188907 A1* | 6/2020 | Wilcox .............. G01N 33/6848 |
| 2020/0386759 A1* | 12/2020 | Wilcox ............ G01N 33/57419 |
| 2021/0063410 A1* | 3/2021 | Wilcox .............. G01N 33/6848 |
| 2021/0208117 A1* | 7/2021 | Murase ................. G01N 30/86 |
| 2022/0139499 A1* | 5/2022 | Xu ......................... G16H 50/20 |
| | | 435/23 |

FOREIGN PATENT DOCUMENTS

| | | |
|---|---|---|
| WO | WO-2017180652 A1 | 10/2017 |
| WO | WO-2018232043 A1 | 12/2018 |

OTHER PUBLICATIONS

International Preliminary Report on Patentability dated Dec. 17, 2019 for International Application No. PCT/US2018/037417.
International Search Report and Written Opinion dated Oct. 31, 2018 for International Application No. PCT/US2018/037417.

\* cited by examiner

TANDEM IDENTIFICATION ENGINE

CROSS-REFERENCE

This application is a national stage entry of International Application No. PCT/US2018/037417, filed Jun. 13, 2018, which claims the benefit of U.S. Provisional Application No. 62/519,294, filed Jun. 14, 2017, which is hereby explicitly incorporated herein by reference in its entirety.

BACKGROUND OF THE INVENTION

Mass spectrometry is an analytical technique capable of identifying molecules in a sample by ionizing the molecules and evaluating their mass to charge ratio. High throughput mass spectrometry involves analyzing complex mixtures composed of thousands of molecular species. The volume of data involved in such analysis complicates the development of faster and more efficient data analysis workflows.

SUMMARY OF THE INVENTION

Disclosed herein are methods and computer systems related to image-based data analysis such as mass spectrometric data analysis. Methods and computer systems herein facilitate the rapid, accurate, and automated analysis of data from samples subjected to mass spectrometry analysis. Faster and/or more efficient mass spectra data analysis is achieved using multiple parallel micro-processes. In some cases, micro-processes are analyzed in parallel through parallel processing using a plurality of micro-processors. Alternatively or in combination, multiple networked computers are leveraged for faster analysis of mass spectrometry data using parallel computing.

Disclosed herein are methods for analyzing mass spectra data. Some such methods comprise at least one of: a) obtaining a plurality of mass spectra data; b) executing a plurality of micro-processes, said micro-processes comprising: i) selecting a first unanalyzed mass spectrum from the plurality of mass spectra data; ii) analyzing said first mass spectrum until a peptide ID is determined; and iii) categorizing said first mass spectrum. A first micro-process and a second micro-process of the plurality of micro-processes operate concurrently or consecutively. Various aspects incorporate one or more of the following elements. The selecting, analyzing, and categorizing the first mass spectrum is in some cases performed by the first micro-process. The plurality of micro-processes optionally further comprises at least one of the following elements: a) selecting a second unanalyzed mass spectrum from the plurality of mass spectra data; b) analyzing said second mass spectrum until a peptide ID is determined; and c) categorizing said second mass spectrum. In some cases, at least one of the selecting, analyzing, and categorizing the second mass spectrum is performed by the second micro-process. The plurality of micro-processes often further comprises at least one of: a) selecting a third unanalyzed mass spectrum from the plurality of mass spectra data; b) analyzing said third mass spectrum until a peptide ID is determined; and c) categorizing said third mass spectrum. The selecting, analyzing, and categorizing the third mass spectrum is usually carried out by a third micro-process. Oftentimes, the first micro-process, the second micro-process, and the third micro-process operate independently. The first micro-process and the second micro-process operate in coordination or independently. The plurality of micro-processes often operates independently and concurrently. The plurality of micro-processes usually comprises selecting, analyzing, and categorizing mass spectra from the plurality of mass spectra data until said plurality of micro-processes is suspended or terminated. In some instances, the plurality of micro-processes continues selecting, analyzing, and categorizing mass spectra until the plurality of mass spectra data has been categorized. Sometimes, the method comprises terminating the first micro-process. Analyzing often comprises running a search of the first mass spectrum in a peptide sequence database. Various searches comprise searching the peptide sequence database for at least one candidate peptide having similar precursor mass. In many cases, the search further comprises obtaining at least one theoretical spectrum for the at least one candidate peptide and scoring the at least one theoretical spectrum based on degree of matching with the first mass spectrum. The peptide ID is sometimes determined based on a highest scoring theoretical spectrum. Categorizing often comprises assigning the peptide ID to the first mass spectrum. Categorizing optionally comprises indicating the first mass spectrum as analyzed. The plurality of micro-processes sometimes comprises at least 10 micro-processes, such as 10, 11, 12, 13, 14, 15, 16, 17, 18, 19, 20, or more than 20 micro-processes. The plurality of micro-processes is typically initiated by a series of nested calls. Oftentimes, each micro-process is run as a background nohup process. The method sometimes further comprises monitoring the plurality of micro-processes. Monitoring often comprises directly observing the plurality of micro-processes on a computing system executing said plurality of micro-processes. Sometimes, monitoring comprises communicating with a computer system executing said plurality of micro-processes using an SQL messaging queue. In many instances, monitoring comprises obtaining a status of at least one micro-process. On certain occasions, a status indicates a micro-process has not been selected, is currently working on an ID, has found a successful ID, or has not found an ID. Monitoring comprises grouping the plurality of micro-processes by status, in various aspects. The method usually further comprises obtaining peptide ID data comprising at least one peptide ID determined by the plurality of micro-processes. Sometimes, the method further comprises analyzing the peptide ID data to determine at least one identified protein. Analyzing the peptide ID data usually comprises performing peptide homology matching. Peptide homology matching typically comprises calculating a protein false discovery rate. The method often further comprises generating an output comprising at least one identified protein. The plurality of mass spectra data sometimes comprises precursor entries comprising mz and abundance values extracted from raw mass spectra data. In various embodiments, the plurality of mass spectra data is stored on a database as a two-dimensional array containing mz and abundance values extracted from raw mass spectrum data. Sometimes, the plurality of mass spectra data is stored on a database, wherein the data is formatted as an isotope reduced array storing mono-isotope mz, abundance, and charge state. The plurality of mass spectra data comprises in some cases at least 1,000 mass spectra and is categorized in no more than 8 hours, or no more than 7 hours, or no more than 6 hours, or no more than 5 hour, or no more than 4 hours, or no more than 3 hours, or no more than 23 hours, or no more than 1 hour. Usually, the plurality of mass spectra data comprises at least 5,000 mass spectra. In many instances, the plurality of mass spectra data comprises at least 10,000 mass spectra. Oftentimes, the plurality of mass spectra data comprises at least 20,000 mass spectra. The plurality of mass spectra data is at least 1 Gigabyte in size, in certain instances. Sometimes, the plurality of mass spectra data is at least 5 Gigabyte in size. The plurality of mass spectra data is often at least 10 Gigabyte in size. The plurality of mass spectra data is occasionally raw mass spectra data. The plurality of mass spectra data usually comprises formatted mass spectra data extracted from raw mass spectra data. In many cases, the plurality of micro-processes is executed by a single core processor. Sometimes, the plurality of micro-processes is executed by a multi-core processor. A single core executes a single micro-process, in various cases. The plurality of micro-processes is often executed by a distributed network of computers. A computer in the distributed network usually executes at least one micro-process. The mass spectra data is typically obtained from a biological sample. The biological sample is oftentimes cell-free blood plasma. Sometimes, the mass spectra data is tandem mass spectra data.

Methods of categorizing mass spectra data are also disclosed herein. Some such methods comprise a) obtaining a plurality of mass spectra data; and b) executing a plurality of micro-processes analyzing and categorizing the plurality of mass spectra data; wherein the plurality of mass spectra data comprises at least 1,000 mass spectra and is categorized in no more than 8 hours. Various aspects incorporate at least one of the following elements. Sometimes, the plurality of mass spectra data is categorized in no more than 4 hours. In some cases, the plurality of mass spectra data is categorized in no more than 1 hour. The plurality of mass spectra data often comprises at least 5,000 mass spectra. The plurality of mass spectra data usually comprises at least 10,000 mass spectra. The plurality of mass spectra data comprises at least 20,000 mass spectra, in certain instances. Oftentimes, the plurality of mass spectra data is at least 1 Gigabyte in size. The plurality of mass spectra data is sometimes at least 5 Gigabyte in size. In certain embodiments, the plurality of mass spectra data is at least 10 Gigabyte in size. The plurality of mass spectra data is occasionally raw mass spectra data. Sometimes, the plurality of mass spectra data comprises formatted mass spectra data extracted from raw mass spectra data. In certain instances, the plurality of micro-processes is executed by a single core processor. Oftentimes, the plurality of micro-processes is executed by a multi-core processor. A single core usually executes a single micro-process. The plurality of micro-processes is sometimes executed by a distributed network of computers. A computer in the distributed network sometimes executes at least one micro-process. Typically, the mass spectra data is obtained from a biological sample. The biological sample is often cell-free blood plasma. The mass spectra data is usually tandem mass spectra data. The plurality of micro-processes often comprise: a) selecting a first unanalyzed mass spectrum from the plurality of mass spectra data; b) analyzing said first mass spectrum until a peptide ID is determined; and c) categorizing said first mass spectrum. Sometimes, the selecting, analyzing, and categorizing the first mass spectrum is carried out by a first micro-process. In various aspects, the plurality of micro-processes further comprises: a) selecting a second unanalyzed mass spectrum from the plurality of mass spectra data; b) analyzing said second mass spectrum until a peptide ID is determined; and c) categorizing said second mass spectrum. Oftentimes, the selecting, analyzing, and categorizing the second mass spectrum is carried out by a second micro-process. The plurality of micro-processes sometimes further comprises: a) selecting a third unanalyzed mass spectrum from the plurality of mass spectra data; b) analyzing said third mass spectrum until a peptide ID is determined; and c) categorizing said third mass spectrum. In some cases, the selecting, analyzing, and categorizing the third mass spectrum is carried out by a third micro-process. Sometimes, the first micro-process, the second micro-process, and the third micro-process operate independently. A first micro-process and a second micro-process of the plurality of micro-processes usually operate concurrently. In many instances, the first micro-process and the second micro-process operate independently. The plurality of micro-processes frequently operates independently and concurrently. The method sometimes further comprises terminating the first micro-process. The plurality of micro-processes often comprises selecting, analyzing, and categorizing mass spectra from the plurality of mass spectra data until said plurality of micro-processes is suspended or terminated. In some instances, the plurality of micro-processes continues selecting, analyzing, and categorizing mass spectra until the plurality of mass spectra data has been categorized. Analyzing usually comprises running a search of the first mass spectrum in a peptide sequence database. The search typically comprises searching the peptide sequence database for at least one candidate peptide with similar precursor mass. Oftentimes, the search further comprises obtaining at least one theoretical spectrum for the at least one candidate peptide and scoring the at least one theoretical spectrum based on degree of matching with the first mass spectrum. In certain aspects, the peptide ID is determined based on a highest scoring theoretical spectrum. The search sometimes comprises matching the first mass spectrum against a library of mass spectra in the peptide sequence database. In certain instances, categorizing comprises assigning the peptide ID to the first mass spectrum. Sometimes, categorizing comprises indicating the first mass spectrum as analyzed. The plurality of micro-processes often comprises at least 10 micro-processes. The plurality of micro-processes sometimes comprises at least 20 micro-processes. In many cases, the plurality of micro-processes is initiated by a series of nested calls. The plurality of micro-processes is typically run as background nohup processes. Oftentimes, the method further comprises monitoring the plurality of micro-processes. In certain aspects, monitoring comprises directly observing the plurality of micro-processes on a computing system executing said plurality of micro-processes. Monitoring sometimes comprises communicating with a computer system executing said plurality of micro-processes using an SQL messaging queue. Monitoring often comprises obtaining a status of at least one micro-process. A status usually indicates a micro-process has not been selected, is currently working on an ID, has found a successful ID, or has not found an ID. Sometimes, monitoring comprises grouping the plurality of micro-processes by status. The method often further comprises obtaining peptide ID data comprising at least one peptide ID determined by the plurality of micro-processes. In many cases, the method further comprises analyzing the peptide ID data to determine at least one identified protein. Analyzing the peptide ID data frequently comprises performing peptide homology matching. Peptide homology often matching comprises calculating a protein false discovery rate. Oftentimes, the method further comprises generating an output comprising at least one identified protein. The plurality of mass spectra data sometimes comprises precursor entries comprising mz and abundance values extracted from raw mass spectra data. In some embodiments, the plurality of mass spectra data is stored on a database as a two-dimensional array containing mz and abundance values extracted from raw mass spectrum data. Oftentimes, the plurality of mass spectra data is stored on a database, wherein the data is formatted as an isotope reduced array storing mono-isotope mz, abundance, and charge state.

The present disclosure also relates to computer systems related to large-scale data image processing, such as data images generated through mass spectrometry analysis. Some such systems comprise at least one processor, a memory, and a software application executable by the at least one processor, said system configured to: a) obtaining a plurality of mass spectra data; b) executing a plurality of micro-processes, said micro-processes comprising: i) selecting a first unanalyzed mass spectrum from the plurality of mass spectra data; ii) analyzing said first mass spectrum until a peptide ID is determined; and iii) categorizing said first mass spectrum; wherein a first micro-process and a second micro-process of the plurality of micro-processes operate concurrently. Various aspects incorporate at least one of the following elements. Sometimes, the selecting, analyzing, and categorizing the first mass spectrum is performed by the first micro-process. In certain cases, the plurality of micro-processes further comprises: a) selecting a second unanalyzed mass spectrum from the plurality of mass spectra data; b) analyzing said second mass spectrum until a peptide ID is determined; and c) categorizing said second mass spectrum. The selecting, analyzing, and categorizing the second mass spectrum is often performed by the second micro-process. The plurality of micro-processes often further comprises: a) selecting a third unanalyzed mass spectrum from the plurality of mass spectra data; b) analyzing said third mass spectrum until a peptide ID is determined; and c) categorizing said third mass spectrum. In various aspects, the selecting, analyzing, and categorizing the third mass spectrum is carried out by a third micro-process. The first micro-process, the second micro-process, and the third micro-process often operate independently. The first micro-process and the second micro-process typically operate independently. The plurality of micro-processes operates independently and concurrently, in many instances. The plurality of micro-processes sometimes comprises selecting, analyzing, and categorizing mass spectra from the plurality of mass spectra data until said plurality of micro-processes is suspended or terminated. Oftentimes, the plurality of micro-processes continues selecting, analyzing, and categorizing mass spectra until the plurality of mass spectra data has been categorized. In many cases, the system is further configured to terminating the first micro-process. Sometimes, analyzing comprises running a search of the first mass spectrum in a peptide sequence database. The search usually comprises searching the peptide sequence database for at least one candidate peptide with similar precursor mass. The search often further comprises obtaining at least one theoretical spectrum for the at least one candidate peptide and scoring the at least one theoretical spectrum based on degree of matching with the first mass spectrum. Sometimes, the peptide ID is determined based on a highest scoring theoretical spectrum. In various cases, the search comprises matching the first mass spectrum against a library of mass spectra in the peptide sequence database. Categorizing sometimes comprises assigning the peptide ID to the first mass spectrum. Oftentimes, categorizing comprises indicating the first mass spectrum as analyzed. The plurality of micro-processes usually comprises at least 10 micro-processes. In some instances, the plurality of micro-processes comprises at least 20 micro-processes. Usually, the plurality of micro-processes is initiated by a series of nested calls. In certain embodiments, each micro-process is run as a background nohup process. Oftentimes, the computer system is further configured to monitoring the plurality of micro-processes. Monitoring often comprises directly observing the plurality of micro-processes on a computing system executing said plurality of micro-processes. Monitoring frequently comprises communicating with a computer system executing said plurality of micro-processes using an SQL messaging queue. Sometimes, monitoring comprises obtaining a status of at least one micro-process. In various cases, a status indicates a micro-process has not been selected, is currently working on an ID, has found a successful ID, or has not found an ID. Monitoring often comprises grouping the plurality of micro-processes by status. In certain instances, the computer system is further configured to obtaining peptide ID data comprising at least one peptide ID determined by the plurality of micro-processes. Sometimes, the computer system is further configured to analyzing the peptide ID data to determine at least one identified protein. Analyzing the peptide ID data usually comprises performing peptide homology matching. Oftentimes, peptide homology matching comprises calculating a protein false discovery rate. In certain embodiments, the computer system is further configured to generating an output comprising at least one identified protein. In many cases, the plurality of mass spectra data comprises precursor entries comprising mz and abundance values extracted from raw mass spectra data. Sometimes, the plurality of mass spectra data is stored on a database as a two-dimensional array containing mz and abundance values extracted from raw mass spectrum data. In various cases, the plurality of mass spectra data is stored on a database, wherein the data is formatted as an isotope reduced array storing mono-isotope mz, abundance, and charge state. The plurality of mass spectra data often comprises at least 1,000 mass spectra and is categorized in no more than 8 hours. Sometimes, the plurality of mass spectra data is categorized in no more than 4 hours. The plurality of mass spectra data is occasionally categorized in no more than 1 hour. In some instances, the plurality of mass spectra data comprises at least 5,000 mass spectra. Sometimes, the plurality of mass spectra data comprises at least 10,000 mass spectra. Oftentimes, the plurality of mass spectra data comprises at least 20,000 mass spectra. The plurality of mass spectra data is typically at least 1 Gigabyte in size. Usually, the plurality of mass spectra data is at least 5 Gigabyte in size. In many cases, the plurality of mass spectra data is at least 10 Gigabyte in size. The plurality of mass spectra data is occasionally raw mass spectra data. The plurality of mass spectra data often comprises formatted mass spectra data extracted from raw mass spectra data. Sometimes, the plurality of micro-processes is executed by a single core processor. The plurality of micro-processes is usually executed by a multi-core processor. A single core executes a single micro-process, in many cases. Oftentimes, the plurality of micro-processes is executed by a distributed network of computers. A computer in the distributed network frequently executes at least one micro-process. In certain cases, the mass spectra data is obtained from a biological sample. The biological sample is sometimes cell-free blood plasma. The mass spectra data is usually tandem mass spectra data.

Similarly disclosed herein are computer systems comprising at least one processor, a memory, and a software application executable by the at least one processor, said system configured to: a) obtaining a plurality of mass spectra data; and b) executing a plurality of micro-processes categorizing the plurality of mass spectra data; wherein the plurality of mass spectra data comprises at least 1,000 mass spectra and is categorized in no more than 8 hours. Oftentimes, the plurality of mass spectra data is categorized in no more than 4 hours. In many cases, the plurality of mass spectra data is categorized in no more than 1 hour. The plurality of mass spectra data often comprises at least 5,000 mass spectra. The plurality of mass spectra data sometimes comprises at least 10,000 mass spectra. The plurality of mass spectra data comprises at least 20,000 mass spectra, in various instances. The plurality of mass spectra data is usually at least 1 Gigabyte in size. Typically, the plurality of mass spectra data is at least 5 Gigabyte in size. The plurality of mass spectra data is oftentimes at least 10 Gigabyte in size. In many cases, the plurality of mass spectra data is raw mass spectra data. Sometimes, the plurality of mass spectra data comprises formatted mass spectra data extracted from raw mass spectra data. The plurality of micro-processes is often executed by a single core processor. In other cases, the plurality of micro-processes is executed by a multi-core processor. Typically, a single core executes a single micro-process. The plurality of micro-processes is sometimes executed by a distributed network of computers. Frequently, a computer in the distributed network executes at least one micro-process. The mass spectra data is often obtained from a biological sample. Usually, the biological sample is cell-free blood plasma. The mass spectra data is frequently tandem mass spectra data. In certain embodiments, the plurality of micro-processes comprise: a) selecting a first unanalyzed mass spectrum from the plurality of mass spectra data; b) analyzing said first mass spectrum until a peptide ID is determined; and c) categorizing said first mass spectrum. Oftentimes, the selecting, analyzing, and categorizing the first mass spectrum is carried out by a first micro-process. In certain cases, the plurality of micro-processes further comprises: a) selecting a second unanalyzed mass spectrum from the plurality of mass spectra data; b) analyzing said second mass spectrum until a peptide ID is determined; and c) categorizing said second mass spectrum. The selecting, analyzing, and categorizing the second mass spectrum is sometimes carried out by a second micro-process. Sometimes, the plurality of micro-processes further comprises: a) selecting a third unanalyzed mass spectrum from the plurality of mass spectra data; b) analyzing said third mass spectrum until a peptide ID is determined; and c) categorizing said third mass spectrum. The selecting, analyzing, and categorizing the third mass spectrum is carried out by a third micro-process, in certain embodiments. Oftentimes, the first micro-process, the second micro-process, and the third micro-process operate independently. In some cases, a first micro-process and a second micro-process of the plurality of micro-processes operate concurrently. Sometimes, the first micro-process and the second micro-process operate independently. In various instances, the plurality of micro-processes operates independently and concurrently. The computer system is often further configured to terminating the first micro-process. The plurality of micro-processes frequently comprises selecting, analyzing, and categorizing mass spectra from the plurality of mass spectra data until said plurality of micro-processes is suspended or terminated. In various cases, the plurality of micro-processes select, analyze, and categorize mass spectra until the plurality of mass spectra data has been categorized. Analyzing typically comprises running a search of the first mass spectrum in a peptide sequence database. The search usually comprises searching the peptide sequence database for at least one candidate peptide with similar precursor mass. Oftentimes, the search further comprises obtaining at least one theoretical spectrum for the at least one candidate peptide and scoring the at least one theoretical spectrum based on degree of matching with the first mass spectrum. The peptide ID is often determined based on a highest scoring theoretical spectrum. The search usually comprises matching the first mass spectrum against a library of mass spectra in the peptide sequence database. In many cases, categorizing comprises assigning the peptide ID to the first mass spectrum. Sometimes, categorizing comprises indicating the first mass spectrum as analyzed. The plurality of micro-processes comprises at least 10 micro-processes, in many instances. The plurality of micro-processes often comprises at least 20 micro-processes. The plurality of micro-processes is typically initiated by a series of nested calls. The plurality of micro-processes is sometimes run as background nohup processes. In some cases, the computer system is further configured for monitoring the plurality of micro-processes. Sometimes, monitoring comprises directly observing the plurality of micro-processes on a computing system executing said plurality of micro-processes. Monitoring occasionally comprises communicating with a computer system executing said plurality of micro-processes using an SQL messaging queue. In some embodiments, monitoring comprises obtaining a status of at least one micro-process. A status typically indicates a micro-process has not been selected, is currently working on an ID, has found a successful ID, or has not found an ID. Oftentimes, monitoring comprises grouping the plurality of micro-processes by status. The computer system is sometimes further configured to obtaining peptide ID data comprising at least one peptide ID determined by the plurality of micro-processes. In certain instances, the computer system is further configured to analyzing the peptide ID data to determine at least one identified protein. Analyzing the peptide ID data usually comprises performing peptide homology matching. Typically, peptide homology matching comprises calculating a protein false discovery rate. In many instances, the computer system is further configured to generating an output comprising at least one identified protein. The plurality of mass spectra data sometimes comprises precursor entries comprising mz and abundance values extracted from raw mass spectra data. In various aspects, the plurality of mass spectra data is stored on a database as a two-dimensional array containing mz and abundance values extracted from raw mass spectrum data. The plurality of mass spectra data is often stored on a database, wherein the data is formatted as an isotope reduced array storing mono-isotope mz, abundance, and charge state.

INCORPORATION BY REFERENCE

All publications, patents, and patent applications mentioned in this specification are herein incorporated by reference to the same extent as if each individual publication, patent, or patent application was specifically and individually indicated to be incorporated by reference. In particular, PCT Publication No. WO2017180652, published on Oct. 19, 2017, is hereby incorporated by reference in its entirety. Also, PCT Publication No. WO2017173390, published on Oct. 5, 2017, is herein incorporated by reference in its entirety.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
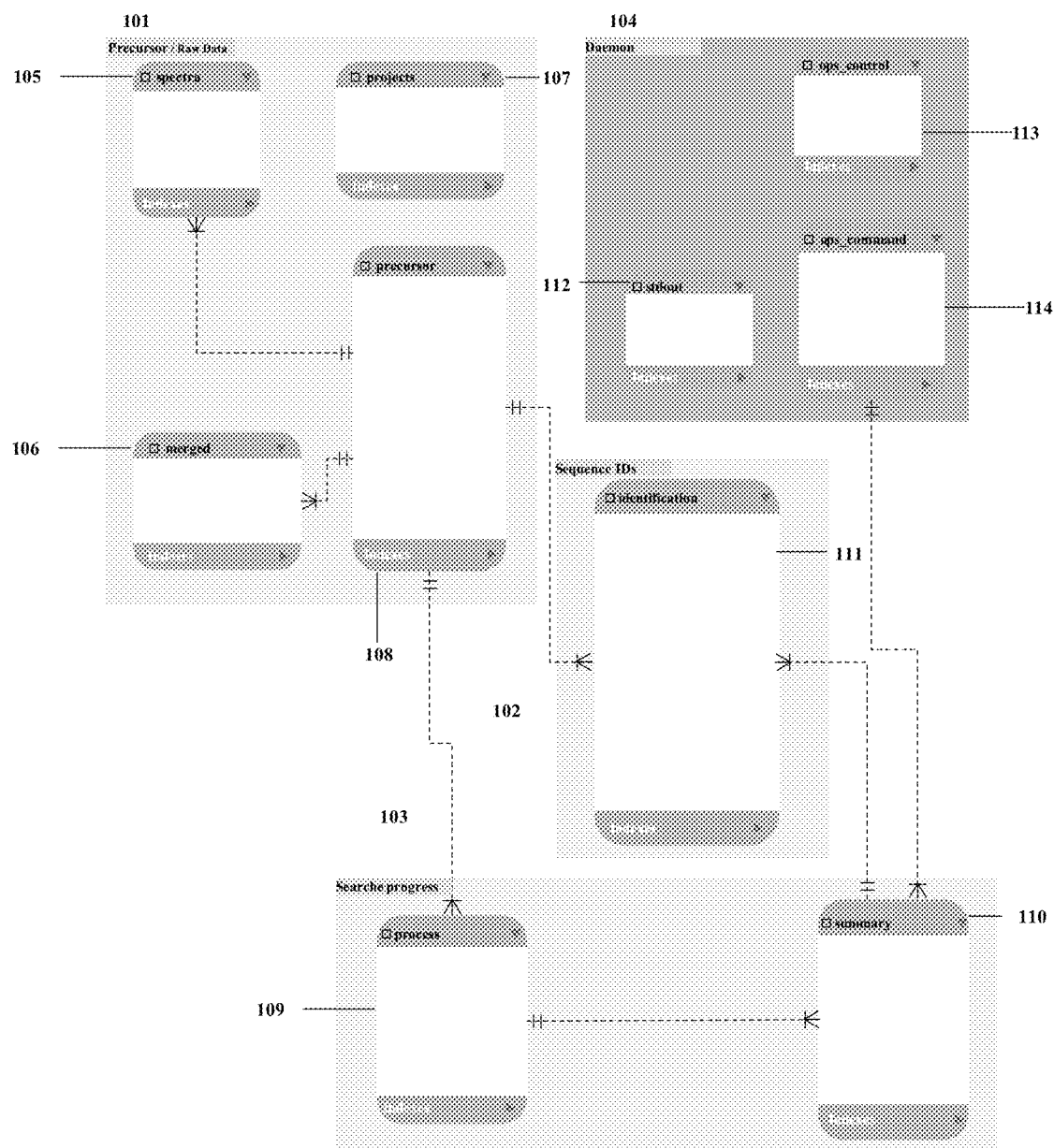
FIG. 1 shows a mass spectra database having an SQL data structure.

Processing large-scale image datasets such as those generated through mass spectrometric analysis of samples such as protein samples remains challenging. Often, even when a wet-lab workflow is running efficiently, data analysis is slowed by the technical challenges associated with processing the data images so as to extract meaningful information regarding relative or absolute sample constituent levels in the mass spectrometric output data. Provided herein are platforms, systems, media, and methods that perform image-based data analysis so as to address this and comparable problems in high-throughput image data analysis. The data analysis typically entails analysis of mass spectra data such as tandem mass spectra data of protein samples. Data analysis is often performed using a plurality of micro-processes. In some cases, the plurality of micro-processes enables rapid analysis of mass spectra data. Data analysis often takes place on a computer system having at least one database and at least one processor. In some cases, the computer system has multiple cores or processors. Alternatively or in combination, the computer system includes a plurality of computers on a distributed network. The data such as mass spectra data is usually uploaded and stored in an appropriate format on a database accessible by the plurality of micro-processes. The systems and methods described herein usually use multiple micro-processes, so as to increase the speed and efficiency of mass spectra data analysis, overcoming the data analysis bottleneck that hampers many mass spectrometry workflows. Instead of relying on a single process for sequential data analysis, multiple parallel micro-processes are able to select individual mass spectra for concurrent analysis in some exemplary embodiments. Oftentimes, a micro-process works independently from other micro-process(es) to identify at least one peptide corresponding to a mass spectrum. An individual micro-process is able to select a mass spectrum from the mass spectra data stored on a database and analyze the mass spectrum to generate a peptide ID. Typically, the analysis includes searching the mass spectrum against a library of peptide sequences, which is optionally stored on a second database. Typically, the plurality of micro-processes continues to analyze mass spectra independently and in parallel. Oftentimes, the data analysis is capable of being monitored. After completion of data analysis, peptide ID data is usually downloaded and subject to protein assembly and accounting to reconstruct the protein components of the sample. Under this approach, the use of multiple parallel micro-processes enables a large data set comprised of thousands of unique mass spectra to be analyzed more rapidly than with a single micro-process.

The platforms, systems, media, and methods provided herein are particularly useful in tandem mass spectrometry. Tandem mass spectrometry has become a useful tool for evaluating complex protein samples, and is often used for protein sequencing. For example, tandem mass spectrometry samples often include protein complexes such as those isolated by co-immunoprecipitation. Because of the sheer variety of protein sequences coupled with various possible post-translational modifications, tandem mass spectrometry data is complicated and difficult to analyze. For example, tandem mass spectrometry of a complex protein sample is capable of generating large data sets of tens of thousands or more of mass spectra. Therefore, the improvements to mass spectrometry data analysis workflow described herein are useful for addressing the burgeoning size and complexity of mass spectra data.

The use of multiple micro-processes for mass spectra analysis described herein is implemented on a computer system having a single processor or core or having multiple processors or cores. When a single processor or core is used, multiple micro-processes are usually executed on a single processor or core using multithreading, which subdivides specific operations in a single application into individual threads that run in parallel. In some cases, data analysis is performed using parallel processing in which the plurality of micro-processes is executed by a plurality of processors in a computing system. Oftentimes, the use of multiple processors enables improved speed of data analysis compared to a single core. In addition, this approach is optionally implemented using distributed computing in which a plurality of micro-processes is executed by multiple computers in a distributed network that makes up a computing system or network. A computer in the network taking part in the data analysis is able to execute at least one micro-process to analyze mass spectra data to generate peptide ID(s). Usually, the peptide IDs found for analyzed mass spectra are then uploaded or communicated to a database. The database often provides the mass spectra data and information useful for assigning the data for analysis. For example, the mass spectra data is usually annotated to indicate whether a specific spectrum or data entry has been analyzed, thus preventing redundant analysis. In this way, the distributed computer systems are able to work together toward a common goal of analyzing the entire mass spectra data set.

Time-consuming data analysis bottle-neck in mass spectrometric workflows is often greatly reduced by the platforms, systems, media, and methods described herein. Mass spectra analysis usually entails identification of peptides by searching mass spectra against known peptide spectra in a sequence database. Even high quality mass spectra often remain unidentified for a variety of reasons. For example, an inaccurate charge state or mass to charge ratio may interfere with peptide identification. Post-translational modification or other unexpected chemical changes to molecular species, incomplete sequence databases, or artificially limited search parameters also pose challenges to successful peptide identification. As a result, a single process may be unable to identify a peptide for a particular mass spectrum. The platforms, systems, media, and methods provided herein enable the execution of a plurality of micro-processes for carrying out parallel analysis of mass spectra data. In some cases, the micro-processes are executed across multiple processors or multi-core processor(s). Alternatively, or in combination, the micro-processes are executed across a distributed network of computers. In some instances, the plurality of micro-processes is executed using cloud computing. As a result, the impact of micro-process slowdowns or frozen micro-processes is reduced for the overall data analysis workflow, and speed of analysis is increased, in many instances.

In addition, micro-processes are usually run as background no hangup ("nohup") processes. Nohup processes ignore any hangup signal that is sent by a terminal to warn dependent processes of logout and are able to run in the background while a user continues working on the terminal. A nohup process is able to continue operating even when a user has logged out, for example, of a remote secure shell channel to the computing system(s) running the process. Sometimes, a user is able to remotely log into a computing system to execute a plurality of micro-processes as nohup processes, wherein logging off from the computing system does not cause the micro-processes to automatically terminate. In contrast, hup processes force a user to remain logged in while mass spectrometric workflow computations are carried out since logging out will cause termination of the processes. For example, in the case of core facilities shared by multiple labs, another user may be unable to log onto a computing system to retrieve data, for instance, because that would require logging out the current user and terminating the ongoing data analysis.

In many instances, the platforms, systems, media, and methods for carrying out data analysis workflows disclosed provide increased speed and efficiency of analysis. For example, in the case that a particular spectrum is difficult to analyze due to inaccurate mass to charge ratio, for example, then the delay is limited to that particular micro-process. Meanwhile, the rest of the analysis goes on unhindered. If parallel computing or distributed computing is utilized, then the speed of data analysis is often greatly improved by the effective use of the added processing power. In addition, a user is able to optionally monitor and/or modulate the micro-processes during data analysis. In some cases, a user limits the processing bandwidth and/or the number of micro-processes allocated to spectra analysis. This allows a user to access and use other applications on a computer system carrying out the analysis without having system lag interfere with those other applications. In some cases, a user is able to run the data analysis as a plurality of background nohup micro-processes while logged out of the computer system.

Sample Processing

Methods, databases and computers configured to receive mass spectrometric data as disclosed herein often involve processing mass spectrometric data sets that are spatially, temporally or spatially and temporally large. For example, datasets are generated that in some cases comprise large amounts of mass spectrometric data points per sample collected, are generated from large numbers of collected samples, and are in some cases generated from multiple samples derived from a single individual.

Mass spectra data is obtained by analyzing a sample using mass spectrometry. A number of sample preparation or processing, sample analysis by mass spectrometry, data analysis, and downstream reporting approaches are consistent with the disclosure herein. In particular, PCT Publication No. WO2017180652, published on Oct. 19, 2017, is hereby incorporated by reference in its entirety. Also, PCT Publication No. WO2017173390, published on Oct. 5, 2017, is herein incorporated by reference in its entirety.

Data collection is in some cases facilitated by depositing samples such as dried blood samples (or other readily obtained samples such as urine, sweat, saliva or other fluid or tissue) onto a solid framework such as a solid backing or solid three-dimensional framework. The sample such as a blood sample is deposited on the solid backing or framework, where it is actively or passively dried, facilitating storage or transport from a collection point to a location where it may be processed.

Figure 3:
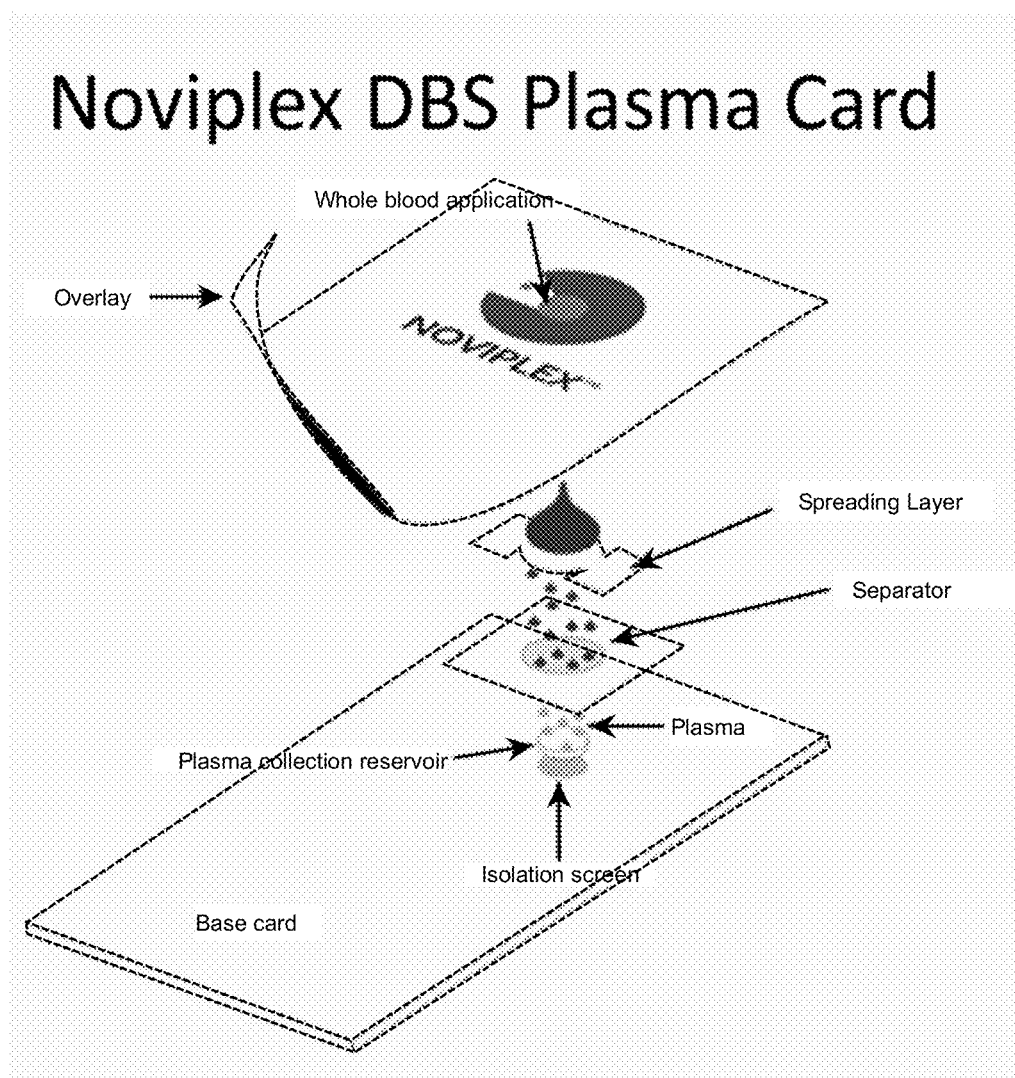
FIG. 3 shows an exemplary Noviplex DBS plasma card.

A sample is usually prepared from a biological sample. Examples of a biological sample include, but are not limited to: urine, stool, tears, whole blood, serum, plasma, dried blood spot, bone marrow, cells, tissue, organ, saliva, buccal swab, cerebrospinal fluid, lymph fluid, skin, and hair. The biological sample can be a dried blood spot collected on a filter device or paper. For example, FIG. 3 shows an exemplary Noviplex DBS plasma card having an overlay, a spreading layer, a separator, a plasma collection reservoir, an isolation screen, and a base card (also shown and described in WO2017180652). Whole blood is applied to a spot on the overlay where it reaches the spreading layer and the separator which allows the plasma to pass through to the plasma collection reservoir. The plasma is stored in the plasma collection reservoir of the plasma card and can be eluted later for mass spectrometric analysis.

As disclosed herein, a number of approaches are available for recovering proteomic or other biomarker information from a dried sample such as a dried blood spot sample. In some cases samples are solubilized, for example in TFE, and subjected to proteolysis to generate fragments to be visualized by mass spectrometric analysis.

A biological sample is usually processed or prepared before being subjected to mass spectrometry analysis. In certain cases, a biological sample is a cell lysate. Alternatively, a biological sample is not a cell lysate such as, for example, cell-free blood plasma. In some cases, sample preparation includes centrifugation, affinity chromatography, magnetic separation, immunopurification, immunoprecipitation, nucleic acid assay, receptor-based assay, colorimetric assay, enzymatic assay, electrophoretic assay, electrochemical assay, spectroscopic assay, cytometric assay, and chromatographic assay. Oftentimes, a biological sample undergoes at least one of fractionation, depletion, enrichment, and dialysis in order to obtain greater purity of the desired molecules (e.g. proteins) while removing undesired molecules (e.g. nucleic acids, lipids, carbohydrates). In some cases, high abundance proteins are depleted. Alternatively, or in combination, target proteins are enriched. Target protein enrichment typically entails enrichment for certain subclasses of proteins based on some property such as a biochemical activity, post-translational modification, or cellular localization (i.e. nuclear versus cytoplasmic). Protein enrichment for post-translational modifications sometimes uses affinity ligands including ion-metal affinity chromatography for phosphorylation or immobilized lectins for glycosylation. Antibodies offer another option for enriching for certain target proteins. A sample usually undergoes dialysis and/or desalting to remove ions and salts that can interfere with mass spectrometry detection.

Oftentimes, the biological sample is digested. Digestion is usually accomplished using an enzyme or nonenzymatic reagent that effects proteolytic cleavage. A number of such reagents are consistent with the disclosure herein, such as trypsin, chymotrypsin, LysC, LysN, AspN, GluC, and ArgC, as well as a number of nonenzymatic proteolytic reagents. Sometimes, the biological sample is also reduced and/or alkylated. Reduction is typically carried out using a reducing agent such as dithiothreitol (DTT), although other reducing agents are consistent with the disclosure herein.

When particular mass spectrometric fragments are of interest or use in analysis, such as a biomarker panel indicative of a health condition status, it is often beneficial to include heavy-labeled or other markers as standard or reference markers as described herein. Markers migrate on a mass spectrometric output at a known position and at a known offset relative to the sample fragments of interest. Inclusion of these markers often leads to 'offset doublets' in mass spectrometric output. By detecting these doublets, one can readily, either personally or through an automated data analysis workflow, identify particular spots of interest to a health condition status among and in addition to the full range of mass spectrometric output data. When the markers have known mass and amount, and optionally when the amount loaded into a sample varies among markers, the markers are also useful as mass standards, facilitating quantification of both the marker-associated fragments and the remaining fragments in the mass spectrometric output.

Standard markers can be introduced to a sample either at collection, during or subsequent to resolubilization, prior to digestion or subsequent to digestion. In some cases a sample collection structure such as a solid backing or a three-dimensional volume is 'pre-loaded' so as to have a standard marker or standard markers present prior to sample collection. Alternately, the standard markers are added to the collection structure subsequent to sample collection, subsequent to sample drying on the structure, during or subsequent to sample collection, during or subsequent to sample resolubilization, or during or subsequent to sample proteolysis treatment. In preferred embodiments, exactly or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 160, 170, 180, 190, 200, 225, 250, 275, 300, or more than 300 standard markers are added to a collection structure prior to sample collection, such that standard processing of the sample results in a mass spectrometric output having the standard markers included in the output without any additional processing of the sample. Accordingly, some methods disclosed herein comprise providing a collection device having sample markers introduced onto the surface prior to sample collection, and some devices or computer systems are configured to receive mass spectrometric data having standard markers included therein, and optionally to identify the mass spectrometric markers and their corresponding native mass fragment.

Figure 4:
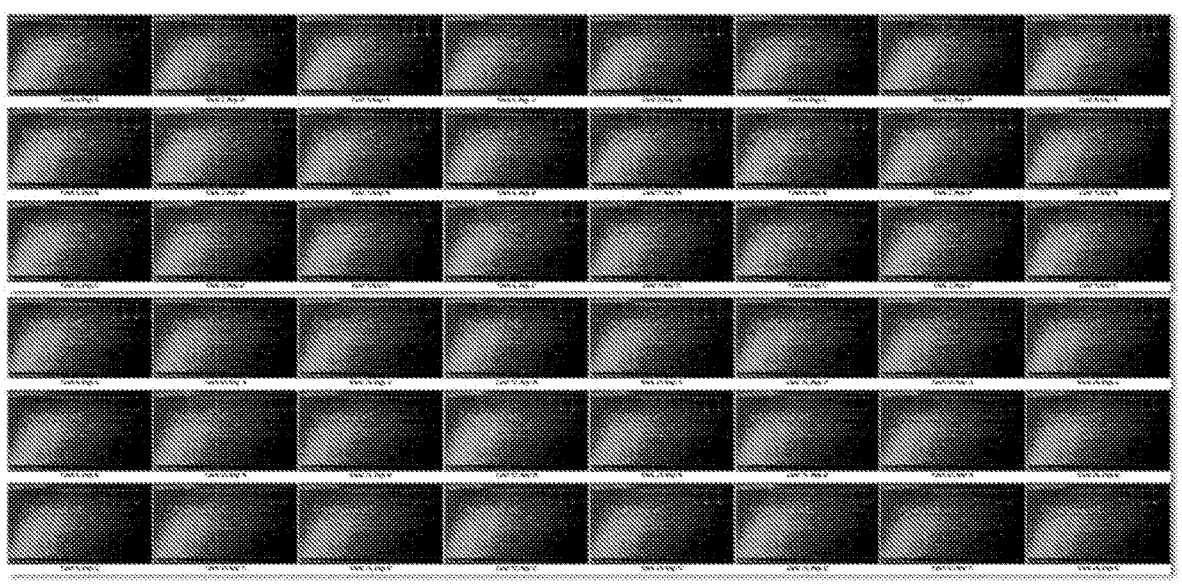
FIG. 4 shows mass spectrometry output graphs resulting from samples subjected to mass spectrometry runs.

A prepared biological sample is then analyzed, such as by mass spectrometry. Mass spectra data is obtained by a number of approaches known in the art, such as analyzing the sample using a particular type of mass spectrometry. Mass spectra data is often obtained using electrospray ionization mass spectrometry, matrix-assisted laser desorption/ionization mass spectrometry, Fourier transform mass spectrometry, ion trap mass spectrometry, time-of-flight (TOF) mass spectrometry, or quadrupole mass spectrometry. FIG. 4 shows 48 mass spectrometry output graphs resulting from 16 dried blood spot (DBS) card samples subjected to three mass spectrometry runs. MS1 data images from 48 injections of a technical replicate variability study are presented. The 16 DBS cards are shown in the columns with their technical replicates in the rows. For each individual MS1 image, the horizontal axis is m/z and the vertical axis is LC time. To show a high-level view of the data quality and reproducibility, a visual representation of the MS1 data from a repeated sampling experiment is shown. Here, each image in the grid shows the data from a single injection on LC time vs. m/z axes, with the color scale representing signal abundance (from black—no signal, to red—high signal). The consistency of the images shows the repeatability of the assay.

Figure 5A:
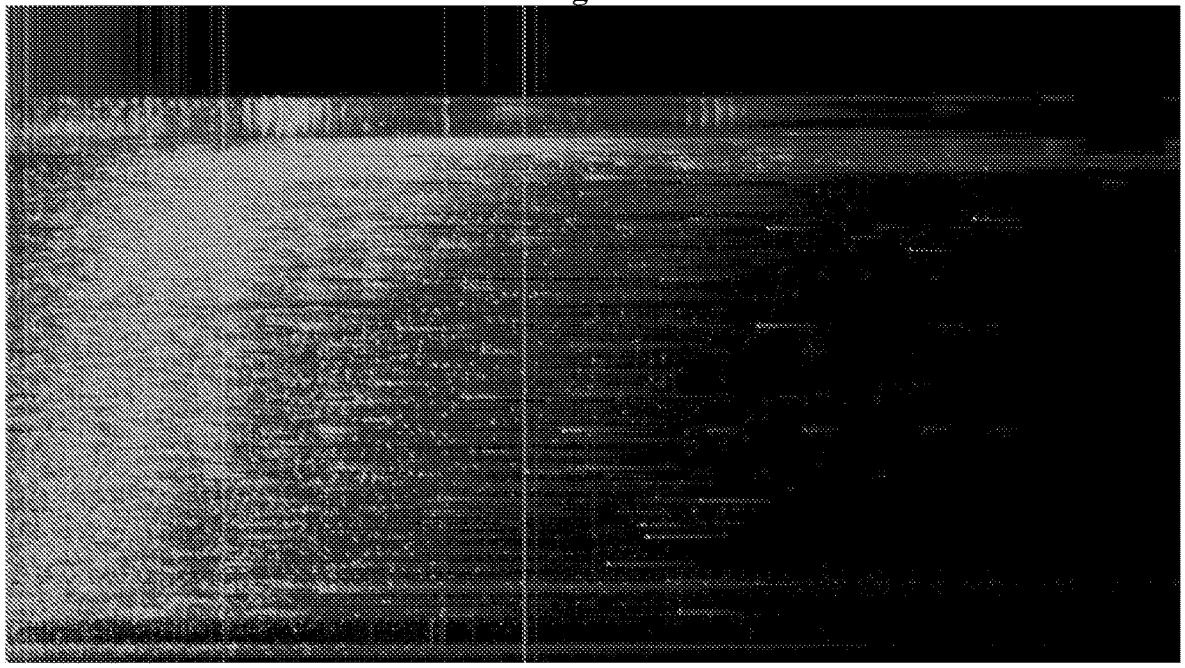
FIG. 5A shows output data of a mass spectrometric analysis.
Figure 5B:
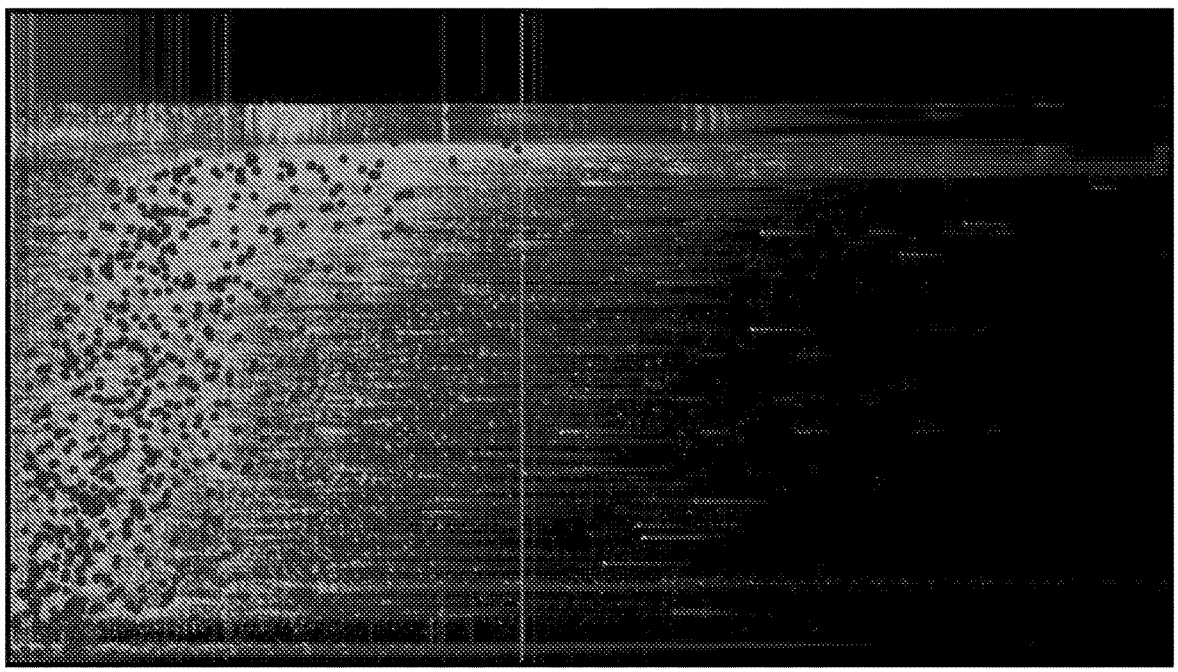
FIG. 5B shows output data as in FIG. 5A with an overlay of positions of added heavy labeled markers.

In some cases, markers such as heavy labeled reference markers are used to enhance detection and/or analysis of native peptides. FIG. 5A shows output data of a mass spectrometric analysis showing more than 10,000 spots. FIG. 5B shows output data of a mass spectrometric analysis as in FIG. 5A with an overlay of positions of added heavy labeled markers depicted as red dots in the graph. These two figures in combination demonstrate how reference markers facilitate identification of native spots in mass spectrometric output Tandem mass spectrometry is especially well suited for analyzing protein samples. Tandem mass spectrometry ionizes sample peptides (precursor ions) and separates those ionized peptides based on mass to charge (m/z) to generate an MS1 scan. The MS1 scan allows peptide precursor ions to be identified. Individual peptide precursor ions are then selected for subsequent fragmentation and detection to generate mass spectra (MS2) for the various fragments that arise from the precursor ion. In some cases, mass spectra data comprises the MS1 scan or information extracted from the MS1 scan such as, for example, the mass to charge ratio (m/z) of a precursor ion that is selected for further analysis. Sometimes, mass spectra data comprises the MS2 scan or information extracted from the MS2 scan such as, for example, m/z peak information. In certain instances, mass spectra data comprises additional information such as at least one of precursor m/z, total ion current, base peak intensity, number of peaks, minimum m/z, maximum m/z, m/z corrected spectra, quality metrics, and de-isotoped spectra.

Computational System for Carrying Out Mass Spectra Data Analysis

Provided herein are systems and methods for analyzing image-based data such as, for example, mass spectrometry data. The mass spectrometry data is often tandem mass spectrometry data. In some cases, the systems and methods are carried out using two resources: database(s) and the computational process. The databases are oftentimes run on a server (i.e. svr_devpipe_u07.api.local), while the computational process (i.e. argc.api.local) is sometimes run off of a local computing system. The database resources are often migrated to another resource. Sometimes, the computational code is migrated, or distributed to additional resources to maximize throughput. As an illustrative example, the computational code is distributed onto a distributed network of computers that combine to execute a plurality of micro-processes for analyzing mass spectra data. This platform is capable of accommodating multiple simultaneous processes such as, for example, up to 40 micro-processes. These simultaneous processes are deployable on the local computing system, or alternatively, on additional resources for maximizing throughput. In the case that an upper limit of simultaneous processes is reached on a given computing system, more parallel processes can be deployed on another instance. If the database drops, suspends, or hangs some of the concurrent connections, leading to unfinished processes, these unfinished processes are optionally located in the database, and manually reset for processing. An exemplar diagram showing the architecture of the databases and the computational code or process is shown below.

| | |
|---|---|
| svr devpipe u07 | argc |
| MongoDB peptide sequence DB | ID Engine runtime |
| Proteomic | HHVM |
| Genomic | PHP |
| MySQL data DB | R |
| Tandem spectra | |
| Peptide sequence IDs | |

The systems and methods disclosed herein typically include one or more databases for storing data. In some cases, a first database stores the mass spectrometry data. The mass spectrometry data can be raw data or formatted data having information extracted from raw data. Oftentimes, the first database is a MySQL database. The first database stores additional information aside from the initial spectrometry data, in some cases. For example, the first database is often capable of storing converted data such as an isotope reduced array having mono-isotope mz, abundance, and charge state. Oftentimes, the first database stores precursor entries having information on precursor ions that are analyzed by tandem mass spectrometry. Usually, the first database stores peptide(s) sequence IDs determined to match up with mass spectra. Sometimes, a second database stores a library of peptide spectra. In many cases, the library includes in silico digested proteins with predicted mass spectra for peptides. In some cases, the library includes all possible peptide spectra. Alternatively, or in combination, the second database includes a constrained library of peptide spectra such as, for example, peptides predicted from the human genome or exome. In some cases, the second database stores peptide sequence data based on the genome, or alternatively, peptide sequence data based on the proteome. In some cases, the second database is a MongoDB database. Sometimes, the first database contains the experimental mass spectra data generated by the mass spectrometry analyzer(s), while the second database contains a peptide sequence library for conducting searches with the experimental mass spectra data to generate peptide IDs. The first and second databases are usually run on the same server or on multiple servers. In various aspects, the ID Engine is operated using at least three resources: a peptide sequence database (e.g. MongoDB), a mass spectra database (e.g. MySQL SpectralDB), and the software code for the ID Engine (e.g. PHP code). Sometimes, dependencies include: PHP 5.5+, with MySQL and MongoDB extensions; HHVM, with at least MySQL extensions installed, R 3.0+ with default installed packages.

FIG. 1 shows one embodiment of a mass spectra database having a SQL data structure. The data or information stored in the database is divided into the mass spectra data 201, the sequence IDs 102, the search progress 103, and the daemon program 104 (runs as a background process). The mass spectra data 201 includes at least one of spectra 105, merged data 106, projects 107, and precursor 108. Spectra 105 includes information on mass spectra obtained by mass spectrometry such as, for example, tandem mass spectrometry. The mass spectra includes raw and/or formatted data. Spectra 105 includes at least one of precursor_pk INT, mz_tbl LONGTEXT, iso_tbl LONGTEXT, and pk INT. Merged data 106 includes multiple spectra that are merged, for example, when the spectra arise from the same precursor ion. Merged data 106 includes at least one of pk INT, precursor_pk INT, and merged_precursor_pk INT. Projects 107 includes information on a particular project or multiple projects. Projects 107 include pk INT, project_name VARCHAR, file_name VARCHAR. Precursor 108 includes information extracted from mass spectra data or obtained by processing mass spectra data. Precursor 108 includes at least one of file_name VARCHAR, scan_no INT, mass FLOAT, charge INT, elution_sec INT, elution_percentb FLOAT, int_noise FLOAT, in_signal FLOAT, tqs_n FLOAT, tqs_p FLOAT, and pk INT.

The sequence ID 102 includes identification 111 (e.g. a peptide identification/ID). The identification 111 includes peptide ID information determined for a given mass spectrum such as, for example, the peptide sequence and a p-value for the match. The identification 111 includes at least one of precursor_pk INT, summary_pk INT, sequence VARCHAR, sequence_ptm VARCHAR, mass_neutral FLOAT, prec_eppm FLOAT, frag_eppm_mean FLOAT, frag_eppm_sd FLOAT, frag_dot_inter INT, match_pval FLOAT, search_n INT, and pk INT.

The search progress 103 includes at least one of the process 109 and the summary 110. The process 100 provides information on the search carried out for a particular spectrum such as the precursor rank or status of the search. The process 109 includes at least one of precursor_pk INT, precursor_rank TINYINT, status INT, progress INT, process_id VARCHAR, and pk INT. The summary 110 provides information summarizing the search such as, for example, the runtime of the search. The summary 110 includes at least one of process_pk INT, command_pk INT, stdout_pk INT, process_id VARCHAR, runtime TIMESTAMP, duration_sec INT, and pk INT.

The daemon 104 includes at least one of stdout 112, ops_control 113, and ops_command 114. Stdout 112 provides standard output that may include at least one of pk INT, and stdout LONGTEXT. Ops_control 113 includes at least one of pk INT, var VARCHAR, and val VARCHAR. Ops_command 114 includes at least one of name VARCHAR, arguments TINYTEXT, runorder INT, active TINYINT, and pk INT.

Disclosed herein are methods for analyzing mass spectra data. Some such methods comprise: a) obtaining a plurality of mass spectra data; b) executing a plurality of micro-processes, said micro-processes comprising: i) selecting a first unanalyzed mass spectrum from the plurality of mass spectra data; ii) analyzing said first mass spectrum until a peptide ID is determined; and iii) categorizing said first mass spectrum; wherein a first micro-process and a second micro-process of the plurality of micro-processes operate concurrently. Such methods are usually carried out by a computer system having at least one processor. In some cases, the plurality of micro-processes is executed by a plurality of processors. A processor is often a multi-core processor comprising a plurality of cores. A multi-core processor refers to a single computing component with at least two processing units or cores that are capable of independently executing program instructions. For example, a multi-core processor usually comprises at least 2 cores, 4 cores, 8 cores, 16 cores, 32 cores, 64 cores, or 128 cores. Oftentimes, the plurality of micro-processes is executed by at least one multi-core processor or a plurality of processors in a single computer. Sometimes, each core executes a single micro-process for performing data analysis. As an illustrative example, a multi-core processor comprising 4 cores executes 4 micro-processes with each micro-process executed by a corresponding core. The plurality of processors or the multi-core processor is typically located in a computer. In some cases, the plurality of processors is located in a massively parallel supercomputer. Oftentimes, the plurality of micro-processes is executed by at least 1 processor, at least 2 processors, at least 4 processors, at least 6 processors, at least 8 processors, at least 10 processors, at least 20 processors, at least 30 processors, at least 40 processors, at least 50 processors, at least 60 processors, at least 70 processors, at least 80 processors, at least 90 processors, at least 100 processors, at least 200 processors, at least 300 processors, at least 400 processors, at least 500 processors, at least 600 processors, at least 700 processors, at least 800 processors, at least 900 processors, or at least 1000 processors.

In some cases, a distributed network of computers executes the plurality of micro-processes. Distributed networking allows computer programming and/or data that is being analyzed to be spread out across more than one computer and is typically implemented over a computer network. The assignment of data or data analysis workload is optionally dependent on the computing capability of the computers in the network. For example, a slower performing computer is assigned a proportionally smaller portion of the data analysis workload compared to a faster computer in the network, in many instances. Sometimes, the data analysis is dynamically assigned in real-time on a per-spectrum basis rather than being allocated beforehand. As an example, a computer in the network obtains a first mass spectrum for analysis from a mass spectra database, and upon completing analysis, retrieves an unanalyzed second mass spectrum from the database. Another computer in the network would not retrieve the first or second mass spectrum for analysis since those spectra would be categorized as analyzed or work-in-progress by the database. This approach synchronizes the data analysis performed by computers in the network and avoids redundant analyses. The plurality of micro-processes is often executed by a network of 2 computers to 50,000 computers. In some cases, the plurality of micro-processes is executed by a network of at least 2 computers. Sometimes, the plurality of micro-processes is executed by a network of at most 50,000 computers.

In certain instances, the plurality of micro-processes is executed by a network of at least 2 computers, at least 4 computers, at least 6 computers, at least 8 computers, at least 10 computers, at least 20 computers, at least 30 computers, at least 40 computers, at least 50 computers, at least 60 computers, at least 70 computers, at least 80 computers, at least 90 computers, at least 100 computers, at least 200 computers, at least 300 computers, at least 400 computers, at least 500 computers, at least 600 computers, at least 700 computers, at least 800 computers, at least 900 computers, at least 1000 computers, at least 5000 computers, at least 10000 computers, at least 20000 computers, at least 30000 computers, at least 40000 computers, or at least 50000 computers.

Data Upload

In many cases, mass spectra data is uploaded onto a mass spectra database for analysis. The mass spectra data is often tandem mass spectra data such as for protein samples. Typically, the data is uploaded and stored in a specific format. Tandem mass spectral data is often formatted as MGF data (Mascot generic format). Sometimes, mass spectral data is formatted as JCAMP-DX, ANDI-MS, mzData, mzXML, mzML, BAF, FID, YEP, WIFF, t2d, PKL, RAW, QGD, DAT, MS, qgd, spc, SMS, or XMS. Tandem mass spectral data can be represented in the database by a 64-bot converted JSON representation of a 2-dimensional array containing all of the mz and abundance values extracted from the raw data. In addition, an isotope reduced array containing the mono-isotope mz, abundance, and charge state is optionally stored on the database. Oftentimes, this platform allows the use of any data source that contains extracted peak information. For example, in some cases, MGF formatted mass spectral data is uploaded by extracting each MS2 scan, creating a precursor entry, and uploading the peak list as well as de-isotope and upload quality metrics. Sample flowing commands to upload MGF formatted data are shown:

>ssh argc@argc
>cd ~/Company/Code/bin/upload.
>php MgfToSql.php-path/path/to/mgf_files/

Data Analysis

Platforms, systems, media, and methods disclosed herein allow data analysis to be carried out using a plurality of micro-processes. The use of multiple micro-processes usually enables faster and more efficient generation of output or results. Oftentimes, the data analysis is performed without requiring user supervision. Employment of any of these platforms, systems, media, and methods, individually or in combination, leads to improvements in mass spectrometric workflow, as measured by time, accuracy, and extent of operator supervision required. In some cases, results are generated in real time comparable to that of data input, such that adjustments can be made to a particular workflow as indicated by initial data output.

Disclosed herein are methods of categorizing mass spectra data. Some such methods comprise: a) obtaining a plurality of mass spectra data; and b) executing a plurality of micro-processes analyzing and categorizing the plurality of mass spectra data; wherein the plurality of mass spectra data comprises at least 1,000 mass spectra and is categorized in no more than 8 hours. Such methods are often carried out by a computer system comprising at least one processor. Through practice of the methods or employment of the computer systems as disclosed herein, mass spectra data is analyzed in no more than 24 h, no more than 20 h, no more than 16 h, no more than 12 h, no more than 8 h, no more than 6 h, no more than 5 h, no more than 4 hours, no more than 3 hours, no more than 2 hours, no more than 1 hour, no more than 45 minutes, no more than 30 minutes, no more than 20 minutes, no more than 10 minutes, no more than 5 minutes, or in some cases no more than 4, 3, 2, or 1 minute. In some cases, the mass spectra data is analyzed to completion within a certain time frame while having at least a minimum size. Sometimes, the mass spectra data is at least 10 Megabytes, at least 50 Megabytes, at least 100 Megabytes, at least 200 Megabytes, at least 300 Megabytes, at least 400 Megabytes, at least 500 Megabytes, at least 600 Megabytes, at least 700 Megabytes, at least 800 Megabytes, at least 900 Megabytes, or at least 1000 Megabytes. Sometimes, the mass spectra data is at least 1 Gigabyte, at least 5 Gigabytes, at least 10 Gigabytes, at least 20 Gigabytes, at least 50 Gigabytes, or at least 100 Gigabytes. In some cases, the mass spectra data is at least 1 Terabyte, at least 5 Terabytes, at least 10 Terabytes, at least 20 Terabytes, at least 50 Terabytes, or at least 100 Terabytes. In some cases, the mass spectra data is raw data. Alternatively, the mass spectra data is formatted, processed, or extracted data obtained from raw mass spectra data.

Typically, the mass spectra data is analyzed to completion within a certain time frame while having a minimum number of spectra. In some cases, mass spectra data is analyzed to completion when at least a minimum percentage of the spectra are successfully categorized. For example, in some cases, the mass spectra data is analyzed to completion when at least 50%, at least 60%, at least 70%, at least 80%, at least 90%, at least 95%, or at least 99% of the spectra are categorized. In some cases, a spectra is categorized when the peptide associated with the spectra is identified or if a peptide cannot be identified (e.g., the spectra is categorized as unidentifiable). The systems and methods described herein can enable mass spectra data comprising a minimum number of spectra to be analyzed to completion within a certain time frame. For example, mass spectra data comprising at least 1,000 spectra is analyzed to completion within 1 hour, in some instances. Sometimes, the mass spectra data has 100 spectra to 5,000,000 spectra. Alternatively, the mass spectra data has more than 5,000,000 spectra in certain cases. The mass spectra data usually includes at least 100 spectra. In some cases, the mass spectra data has at least 100 spectra, at least 500 spectra, at least 1,000 spectra, at least 2,000 spectra, at least 3,000 spectra, at least 4,000 spectra, at least 5,000 spectra, at least 10,000 spectra, at least 20,000 spectra, at least 30,000 spectra, at least 40,000 spectra, at least 50,000 spectra, at least 100,000 spectra, at least 200,000 spectra, at least 300,000 spectra, at least 400,000 spectra, at least 500,000 spectra, at least 600,000 spectra, at least 700,000 spectra, at least 800,000 spectra, at least 900,000 spectra, or at least 1,000,000 spectra. In some cases, the mass spectra data has no more than 100 spectra, no more than 500 spectra, no more than 1,000 spectra, no more than 2,000 spectra, no more than 3,000 spectra, no more than 4,000 spectra, no more than 5,000 spectra, no more than 10,000 spectra, no more than 20,000 spectra, no more than 30,000 spectra, no more than 40,000 spectra, no more than 50,000 spectra, no more than 100,000 spectra, no more than 200,000 spectra, no more than 300,000 spectra, no more than 400,000 spectra, no more than 500,000 spectra, no more than 600,000 spectra, no more than 700,000 spectra, no more than 800,000 spectra, no more than 900,000 spectra, or no more than 1,000,000 spectra.

Some systems and methods disclosed herein include a computational process for carrying out analysis of the mass spectra data. Oftentimes, the computational process is carried out by at least one application. The computational process is sometimes referred to as an identification engine or ID Engine. The computational process is run on a computing system separate from the server(s) that maintain the one or more databases, in many instances. The computational process is sometimes run on a single computing system having a single core or multiple cores. Alternatively, or in combination, the computational process is run on multiple computing systems such as in a distributed computing network. The computational process often involves the execution of a plurality of micro-processes for analyzing mass spectra data. The plurality of micro-processes is usually executed at the beginning of the computational process. Alternatively, the micro-processes are not all executed at the beginning of the computational process, and some micro-processes are executed at a later time. For example, in a particular workflow, 10 micro-processes are executed at the start of mass spectra analysis, but the computing system or a user optionally chooses to execute additional micro-processes when the workflow is already in progress. Sometimes, a micro-process is terminated when the workflow is in progress. In some instances, when a micro-process becomes stuck in a loop, the micro-process is optionally terminated, suspended, and/or re-initiated. In some cases, a micro-process selects an individual mass spectrum for analysis. Alternatively, a micro-process occasionally selects a plurality of mass spectra for analysis. Sometimes, a plurality of micro-processes is executed. The number of micro-processes typically varies between analyses of different mass spectra data. In certain instances, the plurality of micro-processes comprises at least 2 micro-processes, at least 3 micro-processes, at least 4 micro-processes, at least 5 micro-processes, at least 6 micro-processes, at least 7 micro-processes, at least 8 micro-processes, at least 9 micro-processes, at least 10 micro-processes, at least 15 micro-processes, at least 20 micro-processes, at least 25 micro-processes, at least 30 micro-processes, at least 35 micro-processes, at least 40 micro-processes, at least 45 micro-processes, at least 50 micro-processes, at least 60 micro-processes, at least 70 micro-processes, at least 80 micro-processes, at least 90 micro-processes, at least 100 micro-processes, at least 200 micro-processes, at least 300 micro-processes, at least 400 micro-processes, at least 500 micro-processes, at least 600 micro-processes, at least 700 micro-processes, at least 800 micro-processes, at least 900 micro-processes, or at least 1,000 or more micro-processes. In certain instances, the plurality of micro-processes comprises no more than 2 micro-processes, no more than 3 micro-processes, no more than 4 micro-processes, no more than 5 micro-processes, no more than 6 micro-processes, no more than 7 micro-processes, no more than 8 micro-processes, no more than 9 micro-processes, no more than 10 micro-processes, no more than 15 micro-processes, no more than 20 micro-processes, no more than 25 micro-processes, no more than 30 micro-processes, no more than 35 micro-processes, no more than 40 micro-processes, no more than 45 micro-processes, no more than 50 micro-processes, no more than 60 micro-processes, no more than 70 micro-processes, no more than 80 micro-processes, no more than 90 micro-processes, no more than 100 micro-processes, no more than 200 micro-processes, no more than 300 micro-processes, no more than 400 micro-processes, no more than 500 micro-processes, no more than 600 micro-processes, no more than 700 micro-processes, no more than 800 micro-processes, no more than 900 micro-processes, or no more than 1,000 or more micro-processes.

The plurality of micro-processes usually comprises a first micro-process and a second micro-process. The first micro-process typically obtains a first mass spectrum from the mass spectra data and analyzes the first mass spectrum to obtain a peptide ID. When the peptide ID is obtained, the first micro-process often uploads or stores the peptide ID in a database and categorizes or classifies the mass spectrum as analyzed. Oftentimes, the first micro-process then obtains an unanalyzed mass spectrum from the mass spectra data and analyzes the unanalyzed mass spectrum to obtain a peptide ID. Usually, the second micro-process obtains a second mass spectrum from the mass spectra data and analyzes the second mass spectrum to obtain a peptide ID. The first and second micro-processes typically work independently and/or concurrently. If one micro-process hangs or freezes, the other micro-process is able to continue analysis without interference. Sometimes, the plurality of micro-processes comprises a third micro-process obtaining a third mass spectrum for analysis to obtain a peptide ID. The third micro-process usually operates independently and concurrently with the first and second mass spectra. In this way, the plurality of micro-processes can include any number of micro-processes simultaneously carrying out data analysis of individual mass spectra.

A micro-process typically performs spectra analysis in a linear process by analyzing a single spectrum before moving onto a next spectrum. For example, a micro-process usually selects a first unanalyzed mass spectrum, analyzes the mass spectrum by searching a peptide sequence database until it determines a peptide ID or is unable to find a peptide ID, categorizes the mass spectrum according to the results of the analysis, and then repeats the process by selecting a second unanalyzed mass spectrum. Oftentimes, the analyzed mass spectrum is tagged, categorized, and/or provided with a status indicator to provide information on the results of the peptide identification process. For example, in some instances, an unanalyzed mass spectrum is categorized as "unanalyzed" or "not yet selected for analysis." Sometimes, a mass spectrum currently being analyzed is categorized or labeled with a status as "under analysis." If a peptide ID has been successfully determined for a mass spectrum, then the spectrum is categorized as having "successful ID," in some instances. Conversely, if no peptide ID has been able to be determined even when the search is ended (e.g. entire library has been searched with no successful match), then the corresponding mass spectrum is sometimes categorized as having "no ID found." Sometimes, the successful peptide ID is associated with the mass spectrum and stored on a database (e.g. a mass spectra SQL database) along with any additional relevant information such as, for example, the peptide sequence, any post-translational modifications found, and/or p-value for the peptide ID match.

In some cases, the plurality of micro-processes is executed using a series of nested calls. The plurality of micro-processes is usually capable of being run at any level of the nested execution. A sample call is shown: DaemonMultiNohup.php>SearchBasic.php>proteinDB.php. In this case, the DaemonMultiNohup.php process starts a new SearchBasic.php process as a background nohup process. In turn, the SearchBasic.php will run until the process is killed, querying the SQL database for new precursors to work on. Once a new precursor+ops_command are identified, SearchBasic.php will pass the arguments onto proteinDB.php to search and score putative peptide sequences against the given tandem mass spectrum.

Sometimes, a single one-off search against a specific spectrum using a specific data base is performed. A sample command script is shown below:
>ssh argc@argc
>cd ~/Company/Code/bin/search/
>php peptideDB.php Examples of commands used to control the operation of the search along with a brief description of said commands are shown in Table 1.

TABLE 1

| Command | Description |
| --- | --- |
| precursor_pk | The SQL primary key to the precursor, running as a micro-process. Values can be set by the messaging queue, running in an open terminal the user may define. |
| summary_pk | The SQL primary key to the output progress prompts, running as a micro-process. This value can be set by the messaging queue, running in an open terminal the user may define, typically as the value 1 for testing. |
| pppm | Precursor error tolerance in parts-per-million, default at 500. |
| fppm | Fragment error tolerance in parts-per-million, default at 125. |
| ptms | The PTM (post-translational modification) class: na = none, com = common, lab = laboratory induced, bio = biologically relevant. ~/Company/Code/peptide_id_engine/ src/php/obj/science/omics/prote/io/Unimod.php |
| combs | The number of PTMs allowed in an all possible Cartesian expansion |
| db | The database to use, source.type.repository source = json, mongo type = table, array, (not specified for MongoDB) repository = json (file), mongo (collection) |

A single micro-process is sometimes executed to work on available, in-ID'd tandem spectra. A sample command script is shown below:
>ssh argc@argc
>cd ~/Company/Code/bin/daemon/
>php SearchBasic.php This above script utilizes a messaging queue built as the process table in the mass spectra database (e.g. MySQL database) to pull down a single spectrum to analyze and executing the first ordered command from the table ops_command. Sometimes, a command allows for varied execution using flags such as those shown in Table 2.

TABLE 2

| Command | Description |
| --- | --- |
| script | Default is active, which will run all active command from ops_command. Alternatively, this can be used to queue a search for a specific process, using the name field from the ops_command table. |
| rte | Sets the run-time environment, hhvm or php. Default is hhvm. |
| sleep | Numeric seconds to sleep until next execution. Default is 1. |

Alternatively, in some instances, a batch of micro-processes is executed to work on available, in-ID'd tandem spectra. A sample command script is shown below:
>ssh argc@argc
>cd ~/Company/Code/bin/daemon/
>php DaemonMultiNohup.php-n 36

This script creates 36 individual micro-processes that will each work on a separate tandem mass spectrum until either an ID is found or there are no more searches to perform.
Monitoring Processing After at least one of the plurality of micro-processes has been executed, the micro-process(es) are optionally monitored throughout the course of the analysis process. There are at least two methods for monitoring the micro-processes. Sometimes, the micro-processes are monitored either by directly observing the processes on the machine, or through the SQL messaging queue. A sample command script for reporting out the process and process ids (PID) for each of the micro-processes is shown:
>ssh argc@argc
>ps aux | egrep "PID|SearchBasic"

The micro-processes are optionally terminated in certain instances. In some cases, a micro-process is terminated when the micro-process is frozen or experiencing extreme slowdown, which can be caused by an infinite loop or resource exhaustion. For example, a sample command script for terminating all of the micro-processes at once is shown:

>ssh argc@argc
>killall-9 php

Sometimes, the progress of the search is monitored by opening a session with the server (e.g. svr_devpipe_u07) using, for example, the MySQL WorkBench. A sample command script is shown:
SELECT status, count(*)
FROM innovation.process GROUP BY status The above script displays the counts for each status group to provide an overview of the progress of the search. This allows a user to view the number of spectra that have not been selected, are currently being worked on, have had a successful ID, or have not had an ID found.

In some cases, an estimated time to completion is provided in response to a request or command. Additional information accessible by monitoring often includes at least one of number of active micro-processes, number of analyzed spectra, number of unanalyzed spectra, number of processors and/or cores performing data analysis, number of computers performing data analysis, or an average (mean, median, or mode) speed of peptide identification (i.e. average time to generate a peptide ID for a given mass spectrum).

Data Download

Peptide ID data is usually downloaded from a database during or after the analysis of the entire mass spectra data set. Oftentimes, peptide ID data is downloaded all mass spectra data has been analyzed. The peptide ID data download is downloaded manually or automatically. In some instances, only a few spectra remain and are being analyzed, but are difficult or impossible to identify. In such instances, a user has the option to download the finished peptide ID data without waiting for analysis of the remaining spectra to be completed.

Protein Assembly and Accounting

Once the mass spectra data has been analyzed to obtain peptide IDs, a homology search and recombination of proteins by peptide frequency is performed in order to determine which proteins are accounted for by the peptides identified from the mass spectra data. A sample command script for carrying out this process is shown:
>ssh argc@argc
>cd ~/Company/Code/bin/search/
>php proteinDB.php-file/path/to/peptide_id_sql_dump.csv This script runs BLASTp for the peptide homology matching, an R script to perform observational frequency analysis, and Fischer's p-value combination for protein FDR (false discovery rate) estimation. Sometimes, the output of this analysis generates two files: the final peptide and spectral assignment to a protein, and the final protein accounting. Oftentimes, the final peptide and spectral assignment to a protein are generated by expanding all spectra/peptide results by the total homology, and then collapsing back down to a single instance based on the final protein accounting or inclusion. A sample output is shown:

/path/to/peptide_id_sql_dump.homology.peptide.csv peptide protein precursor_pk sequence_ptm match_pval 1 AAVAQKPR MYBB_HUMAN 512 AAVAQ[K42.011]PR 4.190e-02

2 AEFAEVSK ALBU_HUMAN 69 AEFAEVSK 1.000e-22

3 ANRPFLVFLR ANT3_HUMAN 400 ANRPFLVFlR 5.310e-18

4 AVLTLDEK A1AT_HUMAN 133 AVLTlDEK 1.000e-22

5 DGLLKK TECT2_HUMAN 387 [D14.016]GLL[K114.043]K 1.000e-22

6 DLLSLPFYHVK HEMO_HUMAN 416 [D14.016]LLSLPFYHVK 3.614e-02 cmd_name sequence_nmass prec_eppm frag_eppm frag_dot_inter frag_dot_rseq 1 simple: obs PTMs 881.509 28.03 19.16 12 0.85714

2 simple: obs PTMs 879.434 24.62 3.68 14 1.00000

3 simple: obs PTMs 1231.720 26.15 2.02 17 0.80952

4 simple: obs PTMs 887.496 19.21 16.48 15 1.00000

5 prot MDB: bio PTMs 800.476 19.27 35.01 10 1.00000

6 prot MDB: bio PTMs 1344.740 25.55 23.18 14 0.58333 frag_dot_riso file_name scan_no mass charge elution_sec 1 0.11001 DBS01U_EQ00006551_160526_003.mgf 512 441.774 2 329

2 0.64901 DBS01U_EQ00006551_160526_003.mgf 69 440.735 2 92

3 0.51010 DBS01U_EQ00006551_160526_003.mgf 400 411.591 3 268

4 0.46463 DBS01U_EQ00006551_160526_003.mgf 133 444.764 2 127

5 0.30409 DBS01U_EQ00006551_160526_003.mgf 387 401.253 2 262

6 0.21451 DBS01U_EQ00006551_160526_003.mgf 416 449.244 3 277 elution_percentb int_noise int_signal tqs_ratio tqs_sprob pk

1 NULL 318.2 1675.5 0.93750 0.9985 512

2 NULL 471.4 12104.9 1.00000 1.0000 69

3 NULL 448.9 6517.8 0.95455 1.0000 400

4 NULL 119.4 1118.2 0.93750 0.9966 133

5 NULL 246.2 2957.1 1.00000 1.0000 387

6 NULL 183.0 1609.3 0.87500 0.9998 416

The output usually includes information such as at least one of the peptide sequence, the protein and species the peptide is derived from, the precursor pk, the peptide sequence with post-translational modification(s), and p-value for the peptide ID match. In many cases, the final protein accounting comprises a list of proteins that are optionally ranked based on p-value reported with the n number of peptide observations. Usually, the peptide observations are based on total number of observed spectra and/or number of unique observed spectra. Protein frequency is accounted by the same peptide, either through repeat measurements or via PTM variants, in many cases. A sample output is shown with protein name and species, the p-value for the protein match, the number of total spectra observed for each protein (n_obs), and the number of unique spectra observed for each protein (n_unique):

/path/to/peptide_id_sql_dump.homology.protein.csv protein protein_pval n_obs n_unique 1 ALBU_HUMAN 1.361154e-52 7 7

2 TRFE_HUMAN 8.086725e-53 7 7

3 SYHC_HUMAN 4.742263e-50 5 5

4 KCRM_HUMAN 1.847921e-61 4 4

5 CATA_HUMAN 3.769694e-34 3 3

6 BID_HUMAN 2.248569e-47 3 3

Digital Processing Device

In some embodiments, the platforms, media, methods and applications for carrying out analysis of image-based data such as mass spectra data described herein include a digital processing device, a processor, or use of the same. In some cases, the digital processing device is a server. Oftentimes, the server comprises at least one database storing mass spectra data and/or peptide sequence information such as, for example, a MySQL database. Sometimes, the server comprises a peptide sequence database such as, for example, a MongoDB. A digital processing device can be a computer. In some cases, a computer is a computing or computer system able to execute a plurality of micro-processes for analyzing mass spectra data. Alternatively, a computer system comprises a plurality of computers in some cases such as, for example, a computer system comprising a distributed network of computers for analyzing mass spectra data. In certain cases, the digital processing device includes one or more hardware central processing units (CPU) that carry out the device's functions. The digital processing device has a single CPU or processor in many cases. Alternatively, in some cases, the digital processing device has multiple CPUs or processors, which are optionally used for analyzing mass spectra data via parallel processing. Sometimes, the digital processing device further comprises an operating system configured to perform executable instructions. The digital processing device is optionally connected a computer network. In many cases, the digital processing device is connected to the Internet such that it accesses the World Wide Web. The digital processing device is optionally connected to a cloud computing infrastructure. Sometimes, the digital processing device is optionally connected to an intranet. The digital processing device is optionally connected to a data storage device, in many cases. In some cases, a digital processing device is a remote digital processing device used by a user to remotely access a computer system to provide instructions for carrying out mass spectra data analysis.

In accordance with the description herein, suitable digital processing devices include, by way of non-limiting examples, server computers, desktop computers, laptop computers, notebook computers, sub-notebook computers, netbook computers, netpad computers, set-top computers, handheld computers, mobile smartphones, tablet computers, and personal digital assistants. In some instances, such digital processing devices make up at least part of a computer network configured to perform analysis of image-based data such as mass spectra data as described herein. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions including the execution of a plurality of micro-processes for performing analysis of image-based data such as mass spectra data. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. The storage and/or memory device is often used to store image-based data such as mass spectra data. In some cases, the device is volatile memory and requires power to maintain stored information. Volatile memory is sometimes used for temporary storage of mass spectra data during data analysis. Oftentimes, the device includes non-volatile memory and retains stored information when the digital processing device is not powered. For example, sometimes, the non-volatile memory comprises flash memory. The non-volatile memory comprises dynamic random-access memory (DRAM), in various cases. Sometimes, the non-volatile memory comprises ferroelectric random access memory (FRAM). In other cases, the non-volatile memory comprises phase-change random access memory (PRAM). In some cases, the non-volatile memory comprises magnetoresistive random-access memory (MRAM). Oftentimes, the device is a storage device including, by way of non-limiting examples, CD-ROMs, DVDs, flash memory devices, magnetic disk drives, magnetic tapes drives, optical disk drives, and cloud computing based storage. In various cases, the storage and/or memory device is a combination of devices such as those disclosed herein.

In some embodiments, the digital processing device includes a display to send visual information to a subject. For example, the subject or user of the digital processing device is able to visually monitor the ongoing analysis such as performance or progress of individual micro-processes shown on the display. Occasionally, the display is a cathode ray tube (CRT). In many cases, the display is a liquid crystal display (LCD). Sometimes, the display is a thin film transistor liquid crystal display (TFT-LCD). In certain cases, the display is an organic light emitting diode (OLED) display. The OLED display is usually a passive-matrix OLED (PMOLED) or active-matrix OLED (AMOLED) display. Sometimes, the display is a plasma display. On occasion, the display is E-paper or E ink. On rare instances, the display is a video projector. In some cases, the display is a combination of devices such as those disclosed herein.

Oftentimes, the digital processing device includes an input device to receive information from a subject. The input device is frequently a keyboard. The input device is sometimes a pointing device including, by way of non-limiting examples, a mouse, trackball, track pad, joystick, or stylus. The input device is often a touch screen or a multi-touch screen. In certain cases, the input device is a microphone to capture voice or other sound input. On occasion, the input device is a video camera or other sensor to capture motion or visual input. The input device is optionally a combination of devices such as those disclosed herein.

Figure 2:
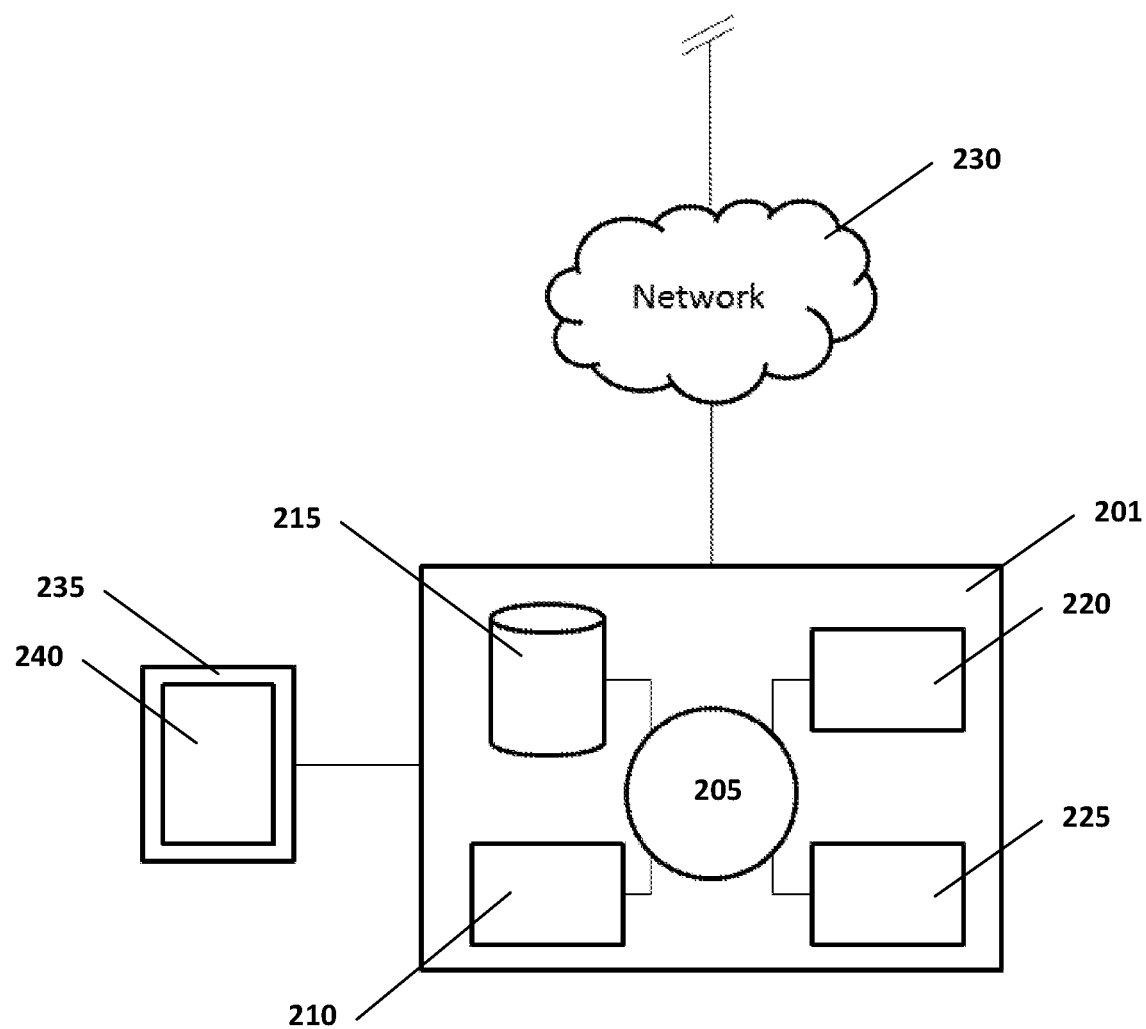
FIG. 2 shows a digital processing device having at least one CPU, a memory, a communication interface, and a display.

Referring to FIG. 2, in a particular embodiment, an exemplary digital processing device 201. In this embodiment, the digital processing device 201 includes at least one central processing unit (CPU, also "processor" and "computer processor" herein) 205, which is a single core or multi core processor, or a plurality of processors for parallel processing. The parallel processing allows for faster analysis of mass spectra data using a plurality of micro-processes compared to linear processing. The digital processing device 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 is usually a data storage unit (or data repository) for storing data. Usually, the digital processing device 201 is operatively coupled to a computer network ("network") 230 with the aid of the communication interface 220. The network 230 is often the Internet, an internet and/or extranet, or an intranet and/or extranet that is in communication with the Internet. The network 230 in some cases is a telecommunication and/or data network. The network 230 typically includes one or more computer servers, which can enable distributed computing, such as cloud computing. The network 230, in some cases with the aid of the device 201, implements a peer-to-peer network, which enables devices coupled to the device 201 to behave as a client or a server. In some cases, a device coupled to the network is able to upload mass spectra data to the network for distributed analysis. The device can upload to a server on the network for managing the distributed analysis by assigning data to specific computers on the network, monitoring progress of the analysis, and receiving and storing the results of the analysis. Alternatively, the device manages the distributed analysis without relying on the network server. In some cases, the data is uploaded as a batch for batch analysis or continuously for real-time analysis. The micro-processes can be executed in the background while other unrelated programs are running.

Continuing to refer to FIG. 2, the CPU 205 is able to execute a sequence of machine-readable instructions including the initiation of a plurality of micro-processes, which can be embodied in a program or software. The instructions are often stored in a memory location, such as the memory 210. The instructions are usually directed to the CPU 205, which can subsequently program or otherwise configure the CPU 205 to implement methods of the present disclosure. Examples of operations performed by the CPU 205 include fetch, decode, execute, and write back. The CPU 205 is often part of a circuit, such as an integrated circuit. One or more other components of the device 201 is optionally included in the circuit. In some cases, the circuit is an application specific integrated circuit (ASIC) or a field programmable gate array (FPGA).

Continuing to refer to FIG. 2, the storage unit 215 is able to store files, such as drivers, libraries and saved programs. The storage unit 215 often stores user data, e.g., user preferences and user programs. The digital processing device 201 sometimes includes one or more additional data storage units that are external, such as located on a remote server that is in communication through an intranet or the Internet.

Continuing to refer to FIG. 2, the digital processing device 201 is often able to communicate with one or more remote computer systems through the network 230. For instance, the device 201 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein are implemented by way of machine (e.g., computer processor) executable code stored on an electronic storage location of the digital processing device 201, such as, for example, on the memory 210 or electronic storage unit 215. The machine executable or machine readable code is often provided in the form of software. During use, the code is usually executed by the processor 205. In some cases, the code is retrieved from the storage unit 215 and stored on the memory 210 for ready access by the processor 205. On occasion, the electronic storage unit 215 is precluded, and machine-executable instructions are stored on memory 210.

Non-Transitory Computer Readable Storage Medium

Oftentimes, the platforms, media, methods and applications described herein include one or more non-transitory computer readable storage media encoded with a program including instructions executable by the operating system of an optionally networked digital processing device to create a plurality of micro-processes for carrying out analysis of image-based data such as mass spectra data. The computer readable storage medium is typically encoded with instructions for performing data analysis using the plurality of micro-processes, which are optionally executed by a plurality of microprocessors and/or a plurality of computing devices in a network. In some cases, a computer readable storage medium is a tangible component of a digital processing device. Occasionally, a computer readable storage medium is optionally removable from a digital processing device. Oftentimes, a computer readable storage medium includes, by way of non-limiting examples, CD-ROMs, DVDs, flash memory devices, solid state memory, magnetic disk drives, magnetic tape drives, optical disk drives, cloud computing systems and services, and the like. The program and instructions are usually permanently, substantially permanently, semi-permanently, or non-transitorily encoded on the media.

Computer Program

Sometimes, the platforms, media, methods and applications described herein include at least one computer program, or use of the same for executing a plurality of micro-processes for carrying out data analysis of image-based data such as mass spectra data. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages. In certain cases, the computer program is configured to execute a plurality of micro-processes for analysis of image-based data using a plurality of micro-processors and/or a plurality of networked computing devices.

The functionality of the computer readable instructions may be combined or distributed as desired in various environments. Typically, a computer program comprises one sequence of instructions. Oftentimes, a computer program comprises a plurality of sequences of instructions configured to be performed in parallel as micro-processes for efficient analysis of image-based data. A computer program is frequently provided from one location. In certain instances, a computer program is provided from a plurality of locations. Sometimes, a computer program includes one or more software modules. A computer program optionally includes, in part or in whole, one or more web applications, one or more mobile applications, one or more standalone applications, one or more web browser plug-ins, extensions, add-ins, or add-ons, or combinations thereof.

Web Application

In some cases, a computer program includes a web application. The web application can provide any of the following: an interface for uploading data for analysis, an interface for monitoring the analysis in real-time (e.g. progress of analysis for individual micro-processes and/or for a batch of data), and an interface for reviewing results of the analysis. In some cases, the web application comprises an interface for performing analysis of uploaded data. For example, a device on a network is able to execute at least one micro-process to analyze uploaded data that has been assigned to the device by a network server responsible for managing the data analysis. In light of the disclosure provided herein, those of skill in the art will recognize that a web application, in various embodiments, utilizes one or more software frameworks and one or more database systems. Sometimes, a web application is created upon a software framework such as Microsoft® .NET or Ruby on Rails (RoR). Oftentimes, a web application utilizes one or more database systems including, by way of non-limiting examples, relational, non-relational, object oriented, associative, and XML database systems. Suitable relational database systems include, by way of non-limiting examples, Microsoft® SQL Server, mySQL™, and Oracle®. Those of skill in the art will also recognize that a web application is written in one or more versions of one or more languages. A web application is capable of being written in one or more markup languages, presentation definition languages, client-side scripting languages, server-side coding languages, database query languages, or combinations thereof. A web application is often written to some extent in a markup language such as Hypertext Markup Language (HTML), Extensible Hypertext Markup Language (XHTML), or eXtensible Markup Language (XML). Sometimes, a web application is written to some extent in a presentation definition language such as Cascading Style Sheets (CSS). Sometimes, a web application is written to some extent in a client-side scripting language such as Asynchronous Javascript and XML (AJAX), Flash® Actionscript, Javascript, or Silverlight®. In various cases, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. On occasion, a web application is written to some extent in a database query language such as Structured Query Language (SQL). Sometimes, a web application integrates enterprise server products such as IBM® Lotus Domino®. On occasion, a web application includes a media player element. The media player element often utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some cases, a computer program includes a mobile application provided to a mobile digital processing device. Sometimes, the mobile application enables the mobile digital processing device to carry out analysis of mass spectra data, for example, as part of a distributed network. In other cases, the mobile application allows the mobile digital processing device to remotely control or send instructions to a computer system for carrying out mass spectra analysis. For example, the mobile application optionally allows a command to be sent to the computer system to initiate, suspend, or terminate at least one micro-process. The mobile application is sometimes provided to a mobile digital processing device at the time it is manufactured. Oftentimes, the mobile application is provided to a mobile digital processing device via a computer network such as the Internet.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, and Samsung® Apps.

Standalone Application

In many cases, a computer program includes a standalone application, which is a program that is run as an independent computer process, not an add-on to an existing process, e.g., not a plug-in. Accordingly, a computer program configured to perform data analysis on image-based data such as mass spectra data is a standalone application, in certain cases. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™ Visual Basic, and VB .NET, or combinations thereof. Compilation is often performed, at least in part, to create an executable program. In some embodiments, a computer program includes one or more executable compiled applications.

Software Modules

In some cases, the platforms, media, methods and applications described herein include software, server, and/or database modules, or use of the same. In view of the disclosure provided herein, software modules are created by techniques known to those of skill in the art using machines, software, and languages known to the art. Sometimes, a software module controls and/or monitors one or more micro-processes. In certain cases, each micro-process is controlled and/or monitored by a single software module. As an example, a plurality of micro-processes each performing analysis of a separate mass spectra is controlled by a corresponding plurality of software modules that monitor the micro-processes for progress or status of the analysis. The software modules disclosed herein are implemented in a multitude of ways. In various instances, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. Typically, the one or more software modules comprise, by way of non-limiting examples, a web application, a mobile application, and a standalone application. Oftentimes, software modules are in one computer program or application. Alternatively, in some instances, software modules are in more than one computer program or application. In many cases, software modules are hosted on one machine. Alternatively, sometimes, software modules are hosted on more than one machine. In certain cases, software modules are hosted on cloud computing platforms. Sometimes, software modules are hosted on one or more machines in one location. Alternatively, some software modules are hosted on one or more machines in more than one location.

Databases

In some embodiments, the platforms, systems, media, and methods disclosed herein include one or more databases, or use of the same, such as, for example, a MySQL database storing mass spectra data and/or a MongoDB peptide sequence database. In view of the disclosure provided herein, those of skill in the art will recognize that many databases are suitable for storage and retrieval of barcode, route, parcel, subject, or network information. In various instances, suitable databases include, by way of non-limiting examples, relational databases, non-relational databases, object oriented databases, object databases, entity-relationship model databases, associative databases, and XML databases. Sometimes, a database is internet-based such as a database located on a distributed computing network configured for mass spectra data analysis via parallel computing. In some cases, a database is web-based. On occasion, a database is cloud computing-based. In certain instances, a database is based on one or more local computer storage devices such as a hard drive of a computing device configured to execute at least one micro-process for analyzing mass spectra data.

Web Browser Plug-in

Sometimes, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. Typically, the toolbar comprises one or more web browser extensions, add-ins, or add-ons. In certain instances, the toolbar comprises one or more explorer bars, tool bands, or desk bands. In some cases, the web browser plug-in adds functionality to the web browser to provide an interface for uploading data for analysis, monitoring ongoing data analysis, reviewing the results of the analysis, or any combination thereof. As an example, a user utilizes a web browser plug-in to upload a batch of mass spectra data to a network server for analysis. The network server then distributes the data to a distributed computer network configured to perform data analysis in parallel, and makes the results available to the user's computing device through the web browser.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some cases, the web browser is a mobile web browser. Mobile web browsers (also called microbrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "about" refers to a variable range about a particular stated value of 10% when the term is applicable. As an example, a value of about 50 would encompass a range from 45 to 55. However, if the value must be an integer value, then "about" will not refer to a variable range that expands the integer value into a range that includes non-integer values. For example, an integer value of about "5" would not refer to 4.5 to 5.5 if the value must be an integer and not a fraction or decimal (e.g. a number of micro-processes cannot have a non-integer value).

Numbered Embodiments

The following embodiments recite nonlimiting permutations of combinations of features disclosed herein. Other permutations of combinations of features are also contemplated. In particular, each of these numbered embodiments is contemplated as depending from or relating to every previous or subsequent numbered embodiment, independent of their order as listed. 1. A method for analyzing mass spectra data, the method comprising: a) obtaining a plurality of mass spectra data; b) executing a plurality of micro-processes, said micro-processes comprising: i) selecting a first unanalyzed mass spectrum from the plurality of mass spectra data; ii) analyzing said first mass spectrum until a peptide ID is determined; and iii) categorizing said first mass spectrum; wherein a first micro-process and a second micro-process of the plurality of micro-processes operate concurrently. 2. The method of embodiment 1, wherein the selecting, analyzing, and categorizing the first mass spectrum is performed by the first micro-process. 3. The method of any of the preceding embodiments such as embodiment 1, wherein the plurality of micro-processes further comprises: a) selecting a second unanalyzed mass spectrum from the plurality of mass spectra data; b) analyzing said second mass spectrum until a peptide ID is determined; and c) categorizing said second mass spectrum. 4. The method of any of the preceding embodiments such as embodiment 3, wherein the selecting, analyzing, and categorizing the second mass spectrum is performed by the second micro-process. 5. The method of any of the preceding embodiments such as embodiment 3, wherein the plurality of micro-processes further comprises: a) selecting a third unanalyzed mass spectrum from the plurality of mass spectra data; b) analyzing said third mass spectrum until a peptide ID is determined; and c) categorizing said third mass spectrum. 6. The method of any of the preceding embodiments such as embodiment 5, wherein the selecting, analyzing, and categorizing the third mass spectrum is carried out by a third micro-process. 7. The method of any of the preceding embodiments such as embodiment 6, wherein the first micro-process, the second micro-process, and the third micro-process operate independently. 8. The method of any of the preceding embodiments such as embodiment 1, wherein the first micro-process and the second micro-process operate independently. 9. The method of any of the preceding embodiments such as embodiment 1, wherein the plurality of micro-processes operates independently and concurrently. 10. The method of any of the preceding embodiments such as embodiment 1, wherein the plurality of micro-processes select, analyze, and categorize mass spectra from the plurality of mass spectra data until said plurality of micro-processes is suspended or terminated. 11. The method of any of the preceding embodiments such as embodiment 1, wherein the plurality of micro-processes continues selecting, analyzing, and categorizing mass spectra until the plurality of mass spectra data has been categorized. 12. The method of any of the preceding embodiments such as embodiment 1, further comprising terminating the first micro-process. 13. The method of any of the preceding embodiments such as embodiment 1, wherein analyzing comprises running a search of the first mass spectrum in a peptide sequence database. 14. The method of any of the preceding embodiments such as embodiment 13, wherein the search comprises searching the peptide sequence database for at least one candidate peptide with similar precursor mass. 15. The method of any of the preceding embodiments such as embodiment 14, wherein the search further comprises obtaining at least one theoretical spectrum for the at least one candidate peptide and scoring the at least one theoretical spectrum based on degree of matching with the first mass spectrum. 16. The method of any of the preceding embodiments such as embodiment 15, wherein the peptide ID is determined based on a highest scoring theoretical spectrum. 17. The method of any of the preceding embodiments such as embodiment 1, wherein categorizing comprises assigning the peptide ID to the first mass spectrum. 18. The method of any of the preceding embodiments such as embodiment 1, wherein categorizing comprises indicating the first mass spectrum as analyzed. 19. The method of any of the preceding embodiments such as embodiment 1, wherein the plurality of micro-processes comprises at least 10 micro-processes. 20. The method of any of the preceding embodiments such as embodiment 1, wherein the plurality of micro-processes comprises at least 20 micro-processes. 21. The method of any of the preceding embodiments such as embodiment 1, wherein the plurality of micro-processes is initiated by a series of nested calls. 22. The method of any of the preceding embodiments such as embodiment 1, wherein each micro-process is run as a background nohup process. 23. The method of any of the preceding embodiments such as embodiment 1, further comprising monitoring the plurality of micro-processes. 24. The method of any of the preceding embodiments such as embodiment 23, wherein monitoring comprises directly observing the plurality of micro-processes on a computing system executing said plurality of micro-processes. 25. The method of any of the preceding embodiments such as embodiment 23, wherein monitoring comprises communicating with a computer system executing said plurality of micro-processes using an SQL messaging queue. 26. The method of any of the preceding embodiments such as embodiment 23, wherein monitoring comprises obtaining a status of at least one micro-process. 27. The method of any of the preceding embodiments such as embodiment 26, wherein a status indicates a micro-process has not been selected, is currently working on an ID, has found a successful ID, or has not found an ID. 28. The method of any of the preceding embodiments such as embodiment 23, wherein monitoring comprises grouping the plurality of micro-processes by status. 29. The method of any of the preceding embodiments such as embodiment 1, further comprising obtaining peptide ID data comprising at least one peptide ID determined by the plurality of micro-processes. 30. The method of any of the preceding embodiments such as embodiment 29, further comprising analyzing the peptide ID data to determine at least one identified protein. 31. The method of any of the preceding embodiments such as embodiment 30, wherein analyzing the peptide ID data comprises performing peptide homology matching. 32. The method of any of the preceding embodiments such as embodiment 31, wherein peptide homology matching comprises calculating a protein false discovery rate. 33. The method of any of the preceding embodiments such as embodiment 30, further comprising generating an output comprising at least one identified protein. 34. The method of any of the preceding embodiments such as embodiment 1, wherein the plurality of mass spectra data comprises precursor entries comprising mz and abundance values extracted from raw mass spectra data. 35. The method of any of the preceding embodiments such as embodiment 1, wherein the plurality of mass spectra data is stored on a database as a two-dimensional array containing mz and abundance values extracted from raw mass spectrum data. 36. The method of any of the preceding embodiments such as embodiment 1, wherein the plurality of mass spectra data is stored on a database, wherein the data is formatted as an isotope reduced array storing mono-isotope mz, abundance, and charge state. 37. The method of any of the preceding embodiments such as embodiment 1, wherein the plurality of mass spectra data comprises at least 1,000 mass spectra and is categorized in no more than 8 hours. 38. The method of any of the preceding embodiments such as embodiment 37, wherein the plurality of mass spectra data is categorized in no more than 4 hours. 39. The method of any of the preceding embodiments such as embodiment 37, wherein the plurality of mass spectra data is categorized in no more than 1 hour. 40. The method of any of the preceding embodiments such as embodiment 37, wherein the plurality of mass spectra data comprises at least 5,000 mass spectra. 41. The method of any of the preceding embodiments such as embodiment 37, wherein the plurality of mass spectra data comprises at least 10,000 mass spectra. 42. The method of any of the preceding embodiments such as embodiment 37, wherein the plurality of mass spectra data comprises at least 20,000 mass spectra. 43. The method of any of the preceding embodiments such as embodiment 37, wherein the plurality of mass spectra data is at least 1 Gigabyte in size. 44. The method of any of the preceding embodiments such as embodiment 37, wherein the plurality of mass spectra data is at least 5 Gigabyte in size. 45. The method of any of the preceding embodiments such as embodiment 37, wherein the plurality of mass spectra data is at least 10 Gigabyte in size. 46. The method of any of the preceding embodiments such as embodiment 37, wherein the plurality of mass spectra data is raw mass spectra data. 47. The method of any of the preceding embodiments such as embodiment 37, wherein the plurality of mass spectra data comprises formatted mass spectra data extracted from raw mass spectra data. 48. The method of any of the preceding embodiments such as embodiment 1, wherein the plurality of micro-processes is executed by a single core processor. 49. The method of any of the preceding embodiments such as embodiment 1, wherein the plurality of micro-processes is executed by a multi-core processor. 50. The method of any of the preceding embodiments such as embodiment 49, wherein a single core executes a single micro-process. 51. The method of any of the preceding embodiments such as embodiment 1, wherein the plurality of micro-processes is executed by a distributed network of computers. 52. The method of any of the preceding embodiments such as embodiment 51, wherein a computer in the distributed network executes at least one micro-process. 53. The method of any of the preceding embodiments such as embodiment 1, wherein the mass spectra data is obtained from a biological sample. 54. The method of any of the preceding embodiments such as embodiment 53, wherein the biological sample is cell-free blood plasma. 55. The method of any of the preceding embodiments such as embodiment 1, wherein the mass spectra data is tandem mass spectra data. 56. A method of categorizing mass spectra data comprising: a) obtaining a plurality of mass spectra data; and b) executing a plurality of micro-processes analyzing and categorizing the plurality of mass spectra data; wherein the plurality of mass spectra data comprises at least 1,000 mass spectra and is categorized in no more than 8 hours. 57. The method of any of the preceding embodiments such as embodiment 56, wherein the plurality of mass spectra data is categorized in no more than 4 hours. 58. The method of any of the preceding embodiments such as embodiment 56, wherein the plurality of mass spectra data is categorized in no more than 1 hour. 59. The method of any of the preceding embodiments such as embodiment 56, wherein the plurality of mass spectra data comprises at least 5,000 mass spectra. 60. The method of any of the preceding embodiments such as embodiment 56, wherein the plurality of mass spectra data comprises at least 10,000 mass spectra. 61. The method of any of the preceding embodiments such as embodiment 56, wherein the plurality of mass spectra data comprises at least 20,000 mass spectra. 62. The method of any of the preceding embodiments such as embodiment 56, wherein the plurality of mass spectra data is at least 1 Gigabyte in size. 63. The method of any of the preceding embodiments such as embodiment 56, wherein the plurality of mass spectra data is at least 5 Gigabyte in size. 64. The method of any of the preceding embodiments such as embodiment 56, wherein the plurality of mass spectra data is at least 10 Gigabyte in size. 65. The method of any of the preceding embodiments such as embodiment 56, wherein the plurality of mass spectra data is raw mass spectra data. 66. The method of any of the preceding embodiments such as embodiment 56, wherein the plurality of mass spectra data comprises formatted mass spectra data extracted from raw mass spectra data. 67. The method of any of the preceding embodiments such as embodiment 56, wherein the plurality of micro-processes is executed by a single core processor. 68. The method of any of the preceding embodiments such as embodiment 56, wherein the plurality of micro-processes is executed by a multi-core processor. 69. The method of any of the preceding embodiments such as embodiment 68, wherein a single core executes a single micro-process. 70. The method of any of the preceding embodiments such as embodiment 56, wherein the plurality of micro-processes is executed by a distributed network of computers. 71. The method of any of the preceding embodiments such as embodiment 70, wherein a computer in the distributed network executes at least one micro-process. 72. The method of any of the preceding embodiments such as embodiment 56, wherein the mass spectra data is obtained from a biological sample. 73. The method of any of the preceding embodiments such as embodiment 72, wherein the biological sample is cell-free blood plasma. 74. The method of any of the preceding embodiments such as embodiment 56, wherein the mass spectra data is tandem mass spectra data. 75. The method of any of the preceding embodiments such as embodiment 56, wherein the plurality of micro-processes comprise: a) selecting a first unanalyzed mass spectrum from the plurality of mass spectra data; b) analyzing said first mass spectrum until a peptide ID is determined; and c) categorizing said first mass spectrum. 76. The method of any of the preceding embodiments such as embodiment 75, wherein the selecting, analyzing, and categorizing the first mass spectrum is carried out by a first micro-process. 77. The method of any of the preceding embodiments such as embodiment 75, wherein the plurality of micro-processes further comprises: a) selecting a second unanalyzed mass spectrum from the plurality of mass spectra data; b) analyzing said second mass spectrum until a peptide ID is determined; and c) categorizing said second mass spectrum. 78. The method of any of the preceding embodiments such as embodiment 77, wherein the selecting, analyzing, and categorizing the second mass spectrum is carried out by a second micro-process. 79. The method of any of the preceding embodiments such as embodiment 77, wherein the plurality of micro-processes further comprises: a) selecting a third unanalyzed mass spectrum from the plurality of mass spectra data; b) analyzing said third mass spectrum until a peptide ID is determined; and c) categorizing said third mass spectrum. 80. The method of any of the preceding embodiments such as embodiment 79, wherein the selecting, analyzing, and categorizing the third mass spectrum is carried out by a third micro-process. 81. The method of any of the preceding embodiments such as embodiment 80, wherein the first micro-process, the second micro-process, and the third micro-process operate independently. 82. The method of any of the preceding embodiments such as embodiment 75, wherein a first micro-process and a second micro-process of the plurality of micro-processes operate concurrently. 83. The method of any of the preceding embodiments such as embodiment 82, wherein the first micro-process and the second micro-process operate independently. 84. The method of any of the preceding embodiments such as embodiment 56, wherein the plurality of micro-processes operates independently and concurrently. 85. The method of any of the preceding embodiments such as embodiment 82, further comprising terminating the first micro-process. 86. The method of any of the preceding embodiments such as embodiment 75, wherein the plurality of micro-processes select, analyze, and categorize mass spectra from the plurality of mass spectra data until said plurality of micro-processes is suspended or terminated. 87. The method of any of the preceding embodiments such as embodiment 75, wherein the plurality of micro-processes continues selecting, analyzing, and categorizing mass spectra until the plurality of mass spectra data has been categorized. 88. The method of any of the preceding embodiments such as embodiment 75, wherein analyzing comprises running a search of the first mass spectrum in a peptide sequence database. 89. The method of any of the preceding embodiments such as embodiment 88, wherein the search comprises searching the peptide sequence database for at least one candidate peptide with similar precursor mass. 90. The method of any of the preceding embodiments such as embodiment 89, wherein the search further comprises obtaining at least one theoretical spectrum for the at least one candidate peptide and scoring the at least one theoretical spectrum based on degree of matching with the first mass spectrum. 91. The method of any of the preceding embodiments such as embodiment 90, wherein the peptide ID is determined based on a highest scoring theoretical spectrum. 92. The method of any of the preceding embodiments such as embodiment 88, wherein the search comprises matching the first mass spectrum against a library of mass spectra in the peptide sequence database. 93. The method of any of the preceding embodiments such as embodiment 75, wherein categorizing comprises assigning the peptide ID to the first mass spectrum. 94. The method of any of the preceding embodiments such as embodiment 75, wherein categorizing comprises indicating the first mass spectrum as analyzed. 95. The method of any of the preceding embodiments such as embodiment 56, wherein the plurality of micro-processes comprises at least 10 micro-processes. 96. The method of any of the preceding embodiments such as embodiment 56, wherein the plurality of micro-processes comprises at least 20 micro-processes. 97. The method of any of the preceding embodiments such as embodiment 56, wherein the plurality of micro-processes is initiated by a series of nested calls. 98. The method of any of the preceding embodiments such as embodiment 56, wherein the plurality of micro-processes is run as background nohup processes. 99. The method of any of the preceding embodiments such as embodiment 56, further comprising monitoring the plurality of micro-processes. 100. The method of any of the preceding embodiments such as embodiment 99, wherein monitoring comprises directly observing the plurality of micro-processes on a computing system executing said plurality of micro-processes. 101. The method of any of the preceding embodiments such as embodiment 99, wherein monitoring comprises communicating with a computer system executing said plurality of micro-processes using an SQL messaging queue. 102. The method of any of the preceding embodiments such as embodiment 99, wherein monitoring comprises obtaining a status of at least one micro-process. 103. The method of any of the preceding embodiments such as embodiment 102, wherein a status indicates a micro-process has not been selected, is currently working on an ID, has found a successful ID, or has not found an ID. 104. The method of any of the preceding embodiments such as embodiment 99, wherein monitoring comprises grouping the plurality of micro-processes by status. 105. The method of any of the preceding embodiments such as embodiment 56, further comprising obtaining peptide ID data comprising at least one peptide ID determined by the plurality of micro-processes. 106. The method of any of the preceding embodiments such as embodiment 105, further comprising analyzing the peptide ID data to determine at least one identified protein. 107. The method of any of the preceding embodiments such as embodiment 106, wherein analyzing the peptide ID data comprises performing peptide homology matching. 108. The method of any of the preceding embodiments such as embodiment 107, wherein peptide homology matching comprises calculating a protein false discovery rate. 109. The method of any of the preceding embodiments such as embodiment 106, further comprising generating an output comprising at least one identified protein. 110. The method of any of the preceding embodiments such as embodiment 56, wherein the plurality of mass spectra data comprises precursor entries comprising mz and abundance values extracted from raw mass spectra data. 111. The method of any of the preceding embodiments such as embodiment 56, wherein the plurality of mass spectra data is stored on a database as a two-dimensional array containing mz and abundance values extracted from raw mass spectrum data. 112. The method of any of the preceding embodiments such as embodiment 56, wherein the plurality of mass spectra data is stored on a database, wherein the data is formatted as an isotope reduced array storing monoisotope mz, abundance, and charge state. 113. A computer system comprising at least one processor, a memory, and a software application executable by the at least one processor, said system configured to: a) obtaining a plurality of mass spectra data; b) executing a plurality of micro-processes, said micro-processes comprising: i) selecting a first unanalyzed mass spectrum from the plurality of mass spectra data; ii) analyzing said first mass spectrum until a peptide ID is determined; and iii) categorizing said first mass spectrum; wherein a first micro-process and a second micro-process of the plurality of micro-processes operate concurrently. 114. The computer system of any of the preceding embodiments such as embodiment 113, wherein the selecting, analyzing, and categorizing the first mass spectrum is performed by the first micro-process. 115. The computer system of any of the preceding embodiments such as embodiment 113, wherein the plurality of micro-processes further comprises: a) selecting a second unanalyzed mass spectrum from the plurality of mass spectra data; b) analyzing said second mass spectrum until a peptide ID is determined; and c) categorizing said second mass spectrum. 116. The computer system of any of the preceding embodiments such as embodiment 115, wherein the selecting, analyzing, and categorizing the second mass spectrum is performed by the second micro-process. 117. The computer system of any of the preceding embodiments such as embodiment 115, wherein the plurality of micro-processes further comprises: a) selecting a third unanalyzed mass spectrum from the plurality of mass spectra data; b) analyzing said third mass spectrum until a peptide ID is determined; and c) categorizing said third mass spectrum. 118. The computer system of any of the preceding embodiments such as embodiment 117, wherein the selecting, analyzing, and categorizing the third mass spectrum is carried out by a third micro-process. 119. The computer system of any of the preceding embodiments such as embodiment 118, wherein the first micro-process, the second micro-process, and the third micro-process operate independently. 120. The computer system of any of the preceding embodiments such as embodiment 113, wherein the first micro-process and the second micro-process operate independently. 121. The computer system of any of the preceding embodiments such as embodiment 113, wherein the plurality of micro-processes operates independently and concurrently. 122. The computer system of any of the preceding embodiments such as embodiment 113, wherein the plurality of micro-processes select, analyze, and categorize mass spectra from the plurality of mass spectra data until said plurality of micro-processes is suspended or terminated. 123. The computer system of any of the preceding embodiments such as embodiment 113, wherein the plurality of micro-processes continues selecting, analyzing, and categorizing mass spectra until the plurality of mass spectra data has been categorized. 124. The computer system of any of the preceding embodiments such as embodiment 113, further comprising terminating the first micro-process. 125. The computer system of any of the preceding embodiments such as embodiment 113, wherein analyzing comprises running a search of the first mass spectrum in a peptide sequence database. 126. The computer system of any of the preceding embodiments such as embodiment 125, wherein the search comprises searching the peptide sequence database for at least one candidate peptide with similar precursor mass. 127. The computer system of any of the preceding embodiments such as embodiment 126, wherein the search further comprises obtaining at least one theoretical spectrum for the at least one candidate peptide and scoring the at least one theoretical spectrum based on degree of matching with the first mass spectrum. 128. The computer system of any of the preceding embodiments such as embodiment 127, wherein the peptide ID is determined based on a highest scoring theoretical spectrum. 129. The computer system of any of the preceding embodiments such as embodiment 125, wherein the search comprises matching the first mass spectrum against a library of mass spectra in the peptide sequence database. 130. The computer system of any of the preceding embodiments such as embodiment 113, wherein categorizing comprises assigning the peptide ID to the first mass spectrum. 131. The computer system of any of the preceding embodiments such as embodiment 113, wherein categorizing comprises indicating the first mass spectrum as analyzed. 132. The computer system of any of the preceding embodiments such as embodiment 113, wherein the plurality of micro-processes comprises at least 10 micro-processes. 133. The computer system of any of the preceding embodiments such as embodiment 113, wherein the plurality of micro-processes comprises at least 20 micro-processes. 134. The computer system of any of the preceding embodiments such as embodiment 113, wherein the plurality of micro-processes is initiated by a series of nested calls. 135. The computer system of any of the preceding embodiments such as embodiment 113, wherein each micro-process is run as a background nohup process. 136. The computer system of any of the preceding embodiments such as embodiment 113, further comprising monitoring the plurality of micro-processes. 137. The computer system of any of the preceding embodiments such as embodiment 136, wherein monitoring comprises directly observing the plurality of micro-processes on a computing system executing said plurality of micro-processes. 138. The computer system of any of the preceding embodiments such as embodiment 136, wherein monitoring comprises communicating with a computer system executing said plurality of micro-processes using an SQL messaging queue. 139. The computer system of any of the preceding embodiments such as embodiment 136, wherein monitoring comprises obtaining a status of at least one micro-process. 140. The computer system of any of the preceding embodiments such as embodiment 139, wherein a status indicates a micro-process has not been selected, is currently working on an ID, has found a successful ID, or has not found an ID. 141. The computer system of any of the preceding embodiments such as embodiment 136, wherein monitoring comprises grouping the plurality of micro-processes by status. 142. The computer system of any of the preceding embodiments such as embodiment 113, further comprising obtaining peptide ID data comprising at least one peptide ID determined by the plurality of micro-processes. 143. The computer system of any of the preceding embodiments such as embodiment 142, further comprising analyzing the peptide ID data to determine at least one identified protein. 144. The computer system of any of the preceding embodiments such as embodiment 143, wherein analyzing the peptide ID data comprises performing peptide homology matching. 145. The computer system of any of the preceding embodiments such as embodiment 144, wherein peptide homology matching comprises calculating a protein false discovery rate. 146. The computer system of any of the preceding embodiments such as embodiment 143, further comprising generating an output comprising at least one identified protein. 147. The computer system of any of the preceding embodiments such as embodiment 113, wherein the plurality of mass spectra data comprises precursor entries comprising mz and abundance values extracted from raw mass spectra data. 148. The computer system of any of the preceding embodiments such as embodiment 113, wherein the plurality of mass spectra data is stored on a database as a two-dimensional array containing mz and abundance values extracted from raw mass spectrum data. 149. The computer system of any of the preceding embodiments such as embodiment 113, wherein the plurality of mass spectra data is stored on a database, wherein the data is formatted as an isotope reduced array storing mono-isotope mz, abundance, and charge state. 150. The computer system of any of the preceding embodiments such as embodiment 113, wherein the plurality of mass spectra data comprises at least 1,000 mass spectra and is categorized in no more than 8 hours. 151. The computer system of any of the preceding embodiments such as embodiment 150, wherein the plurality of mass spectra data is categorized in no more than 4 hours. 152. The computer system of any of the preceding embodiments such as embodiment 150, wherein the plurality of mass spectra data is categorized in no more than 1 hour. 153. The computer system of any of the preceding embodiments such as embodiment 150, wherein the plurality of mass spectra data comprises at least 5,000 mass spectra. 154. The computer system of any of the preceding embodiments such as embodiment 150, wherein the plurality of mass spectra data comprises at least 10,000 mass spectra. 155. The computer system of any of the preceding embodiments such as embodiment 150, wherein the plurality of mass spectra data comprises at least 20,000 mass spectra. 156. The computer system of any of the preceding embodiments such as embodiment 150, wherein the plurality of mass spectra data is at least 1 Gigabyte in size. 157. The computer system of any of the preceding embodiments such as embodiment 150, wherein the plurality of mass spectra data is at least 5 Gigabyte in size. 158. The computer system of any of the preceding embodiments such as embodiment 150, wherein the plurality of mass spectra data is at least 10 Gigabyte in size. 159. The computer system of any of the preceding embodiments such as embodiment 150, wherein the plurality of mass spectra data is raw mass spectra data. 160. The computer system of any of the preceding embodiments such as embodiment 150, wherein the plurality of mass spectra data comprises formatted mass spectra data extracted from raw mass spectra data. 161. The computer system of any of the preceding embodiments such as embodiment 113, wherein the plurality of micro-processes is executed by a single core processor. 162. The computer system of any of the preceding embodiments such as embodiment 113, wherein the plurality of micro-processes is executed by a multi-core processor. 163. The computer system of any of the preceding embodiments such as embodiment 162, wherein a single core executes a single micro-process. 164. The computer system of any of the preceding embodiments such as embodiment 113, wherein the plurality of micro-processes is executed by a distributed network of computers. 165. The computer system of any of the preceding embodiments such as embodiment 164, wherein a computer in the distributed network executes at least one micro-process. 166. The computer system of any of the preceding embodiments such as embodiment 113, wherein the mass spectra data is obtained from a biological sample. 167. The computer system of any of the preceding embodiments such as embodiment 166, wherein the biological sample is cell-free blood plasma. 168. The computer system of any of the preceding embodiments such as embodiment 113, wherein the mass spectra data is tandem mass spectra data. 169. A computer system comprising at least one processor, a memory, and a software application executable by the at least one processor, said system configured to: a) obtaining a plurality of mass spectra data; and b) executing a plurality of micro-processes categorizing the plurality of mass spectra data; wherein the plurality of mass spectra data comprises at least 1,000 mass spectra and is categorized in no more than 8 hours. 170. The computer system of any of the preceding embodiments such as embodiment 169, wherein the plurality of mass spectra data is categorized in no more than 4 hours. 171. The computer system of any of the preceding embodiments such as embodiment 169, wherein the plurality of mass spectra data is categorized in no more than 1 hour. 172. The computer system of any of the preceding embodiments such as embodiment 169, wherein the plurality of mass spectra data comprises at least 5,000 mass spectra. 173. The computer system of any of the preceding embodiments such as embodiment 169, wherein the plurality of mass spectra data comprises at least 10,000 mass spectra. 174. The computer system of any of the preceding embodiments such as embodiment 169, wherein the plurality of mass spectra data comprises at least 20,000 mass spectra. 175. The computer system of any of the preceding embodiments such as embodiment 169, wherein the plurality of mass spectra data is at least 1 Gigabyte in size. 176. The computer system of any of the preceding embodiments such as embodiment 169, wherein the plurality of mass spectra data is at least 5 Gigabyte in size. 177. The computer system of any of the preceding embodiments such as embodiment 169, wherein the plurality of mass spectra data is at least 10 Gigabyte in size. 178. The computer system of any of the preceding embodiments such as embodiment 169, wherein the plurality of mass spectra data is raw mass spectra data. 179. The computer system of any of the preceding embodiments such as embodiment 169, wherein the plurality of mass spectra data comprises formatted mass spectra data extracted from raw mass spectra data. 180. The computer system of any of the preceding embodiments such as embodiment 169, wherein the plurality of micro-processes is executed by a single core processor. 181. The computer system of any of the preceding embodiments such as embodiment 169, wherein the plurality of micro-processes is executed by a multi-core processor. 182. The computer system of any of the preceding embodiments such as embodiment 181, wherein a single core executes a single micro-process. 183. The computer system of any of the preceding embodiments such as embodiment 169, wherein the plurality of micro-processes is executed by a distributed network of computers. 184. The computer system of any of the preceding embodiments such as embodiment 183, wherein a computer in the distributed network executes at least one micro-process. 185. The computer system of any of the preceding embodiments such as embodiment 169, wherein the mass spectra data is obtained from a biological sample. 186. The computer system of any of the preceding embodiments such as embodiment 185, wherein the biological sample is cell-free blood plasma. 187. The computer system of any of the preceding embodiments such as embodiment 169, wherein the mass spectra data is tandem mass spectra data. 188. The computer system of any of the preceding embodiments such as embodiment 169, wherein the plurality of micro-processes comprise: a) selecting a first unanalyzed mass spectrum from the plurality of mass spectra data; b) analyzing said first mass spectrum until a peptide ID is determined; and c) categorizing said first mass spectrum. 189. The computer system of any of the preceding embodiments such as embodiment 188, wherein the selecting, analyzing, and categorizing the first mass spectrum is carried out by a first micro-process. 190. The computer system of any of the preceding embodiments such as embodiment 188, wherein the plurality of micro-processes further comprises: a) selecting a second unanalyzed mass spectrum from the plurality of mass spectra data; b) analyzing said second mass spectrum until a peptide ID is determined; and c) categorizing said second mass spectrum. 191. The computer system of any of the preceding embodiments such as embodiment 190, wherein the selecting, analyzing, and categorizing the second mass spectrum is carried out by a second micro-process. 192. The computer system of any of the preceding embodiments such as embodiment 190, wherein the plurality of micro-processes further comprises: a) selecting a third unanalyzed mass spectrum from the plurality of mass spectra data; b) analyzing said third mass spectrum until a peptide ID is determined; and c) categorizing said third mass spectrum. 193. The computer system of any of the preceding embodiments such as embodiment 192, wherein the selecting, analyzing, and categorizing the third mass spectrum is carried out by a third micro-process. 194. The computer system of any of the preceding embodiments such as embodiment 193, wherein the first micro-process, the second micro-process, and the third micro-process operate independently. 195. The computer system of any of the preceding embodiments such as embodiment 169, wherein a first micro-process and a second micro-process of the plurality of micro-processes operate concurrently. 196. The computer system of any of the preceding embodiments such as embodiment 195, wherein the first micro-process and the second micro-process operate independently. 197. The computer system of any of the preceding embodiments such as embodiment 169, wherein the plurality of micro-processes operates independently and concurrently. 198. The computer system of any of the preceding embodiments such as embodiment 195, further comprising terminating the first micro-process. 199. The computer system of any of the preceding embodiments such as embodiment 188, wherein the plurality of micro-processes select, analyze, and categorize mass spectra from the plurality of mass spectra data until said plurality of micro-processes is suspended or terminated. 200. The computer system of any of the preceding embodiments such as embodiment 188, wherein the plurality of micro-processes select, analyze, and categorize mass spectra until the plurality of mass spectra data has been categorized. 201. The computer system of any of the preceding embodiments such as embodiment 188, wherein analyzing comprises running a search of the first mass spectrum in a peptide sequence database. 202. The computer system of any of the preceding embodiments such as embodiment 201, wherein the search comprises searching the peptide sequence database for at least one candidate peptide with similar precursor mass. 203. The computer system of any of the preceding embodiments such as embodiment 202, wherein the search further comprises obtaining at least one theoretical spectrum for the at least one candidate peptide and scoring the at least one theoretical spectrum based on degree of matching with the first mass spectrum. 204. The computer system of any of the preceding embodiments such as embodiment 203, wherein the peptide ID is determined based on a highest scoring theoretical spectrum. 205. The computer system of any of the preceding embodiments such as embodiment 201, wherein the search comprises matching the first mass spectrum against a library of mass spectra in the peptide sequence database. 206. The computer system of any of the preceding embodiments such as embodiment 188, wherein categorizing comprises assigning the peptide ID to the first mass spectrum. 207. The computer system of any of the preceding embodiments such as embodiment 188, wherein categorizing comprises indicating the first mass spectrum as analyzed. 208. The computer system of any of the preceding embodiments such as embodiment 169, wherein the plurality of micro-processes comprises at least 10 micro-processes. 209. The computer system of any of the preceding embodiments such as embodiment 169, wherein the plurality of micro-processes comprises at least 20 micro-processes. 210. The computer system of any of the preceding embodiments such as embodiment 169, wherein the plurality of micro-processes is initiated by a series of nested calls. 211. The computer system of any of the preceding embodiments such as embodiment 169, wherein the plurality of micro-processes is run as background nohup processes. 212. The computer system of any of the preceding embodiments such as embodiment 169, wherein the computer system is further configured for monitoring the plurality of micro-processes. 213. The computer system of any of the preceding embodiments such as embodiment 212, wherein monitoring comprises directly observing the plurality of micro-processes on a computing system executing said plurality of micro-processes. 214. The computer system of any of the preceding embodiments such as embodiment 212, wherein monitoring comprises communicating with a computer system executing said plurality of micro-processes using an SQL messaging queue. 215. The computer system of any of the preceding embodiments such as embodiment 212, wherein monitoring comprises obtaining a status of at least one micro-process. 216. The computer system of any of the preceding embodiments such as embodiment 215, wherein a status indicates a micro-process has not been selected, is currently working on an ID, has found a successful ID, or has not found an ID. 217. The computer system of any of the preceding embodiments such as embodiment 212, wherein monitoring comprises grouping the plurality of micro-processes by status. 218. The computer system of any of the preceding embodiments such as embodiment 169, further comprising obtaining peptide ID data comprising at least one peptide ID determined by the plurality of micro-processes. 219. The computer system of any of the preceding embodiments such as embodiment 218, further comprising analyzing the peptide ID data to determine at least one identified protein. 220. The computer system of any of the preceding embodiments such as embodiment 219, wherein analyzing the peptide ID data comprises performing peptide homology matching. 221. The computer system of any of the preceding embodiments such as embodiment 220, wherein peptide homology matching comprises calculating a protein false discovery rate. 222. The computer system of any of the preceding embodiments such as embodiment 219, further comprising generating an output comprising at least one identified protein. 223. The computer system of any of the preceding embodiments such as embodiment 169, wherein the plurality of mass spectra data comprises precursor entries comprising mz and abundance values extracted from raw mass spectra data. 224. The computer system of any of the preceding embodiments such as embodiment 169, wherein the plurality of mass spectra data is stored on a database as a two-dimensional array containing mz and abundance values extracted from raw mass spectrum data. 225. The computer system of any of the preceding embodiments such as embodiment 169, wherein the plurality of mass spectra data is stored on a database, wherein the data is formatted as an isotope reduced array storing mono-isotope mz, abundance, and charge state. 226. A method for analyzing mass spectra data, the method comprising: a) obtaining a biological sample; b) subjecting the biological sample to mass spectrometric analysis to generate a plurality of mass spectra data; c) executing a plurality of micro-processes, said micro-processes comprising: i) selecting a first unanalyzed mass spectrum from the plurality of mass spectra data; ii) analyzing said first mass spectrum until a peptide ID is determined; and iii) categorizing said first mass spectrum; wherein a first micro-process and a second micro-process of the plurality of micro-processes operate concurrently. 227. The method of any of the preceding embodiments such as embodiment 226, wherein the selecting, analyzing, and categorizing the first mass spectrum is performed by the first micro-process. 228. The method of any of the preceding embodiments such as embodiment 226, wherein the plurality of micro-processes further comprises: a) selecting a second unanalyzed mass spectrum from the plurality of mass spectra data; b) analyzing said second mass spectrum until a peptide ID is determined; and c) categorizing said second mass spectrum. 229. The method of any of the preceding embodiments such as embodiment 228, wherein the selecting, analyzing, and categorizing the second mass spectrum is performed by the second micro-process. 230. The method of any of the preceding embodiments such as embodiment 228, wherein the plurality of micro-processes further comprises: a) selecting a third unanalyzed mass spectrum from the plurality of mass spectra data; b) analyzing said third mass spectrum until a peptide ID is determined; and c) categorizing said third mass spectrum. 231. The method of any of the preceding embodiments such as embodiment 230, wherein the selecting, analyzing, and categorizing the third mass spectrum is carried out by a third micro-process. 232. The method of any of the preceding embodiments such as embodiment 231, wherein the first micro-process, the second micro-process, and the third micro-process operate independently. 233. The method of any of the preceding embodiments such as embodiment 226, wherein the first micro-process and the second micro-process operate independently. 234. The method of any of the preceding embodiments such as embodiment 226, wherein the plurality of micro-processes operates independently and concurrently. 235. The method of any of the preceding embodiments such as embodiment 226, wherein the plurality of micro-processes select, analyze, and categorize mass spectra from the plurality of mass spectra data until said plurality of micro-processes is suspended or terminated. 236. The method of any of the preceding embodiments such as embodiment 226, wherein the plurality of micro-processes continues selecting, analyzing, and categorizing mass spectra until the plurality of mass spectra data has been categorized. 237. The method of any of the preceding embodiments such as embodiment 226, wherein analyzing comprises running a search of the first mass spectrum in a peptide sequence database. 238. The method of any of the preceding embodiments such as embodiment 237, wherein the search comprises searching the peptide sequence database for at least one candidate peptide with similar precursor mass. 239. The method of any of the preceding embodiments such as embodiment 238, wherein the search further comprises obtaining at least one theoretical spectrum for the at least one candidate peptide and scoring the at least one theoretical spectrum based on degree of matching with the first mass spectrum. 240. The method of any of the preceding embodiments such as embodiment 226, wherein categorizing comprises assigning the peptide ID to the first mass spectrum. 241. The method of any of the preceding embodiments such as embodiment 226, wherein categorizing comprises indicating the first mass spectrum as analyzed. 242. The method of any of the preceding embodiments such as embodiment 226, wherein the plurality of micro-processes comprises at least 10 micro-processes. 243. The method of any of the preceding embodiments such as embodiment 226, wherein the plurality of micro-processes is initiated by a series of nested calls. 244. The method of any of the preceding embodiments such as embodiment 226, wherein each micro-process is run as a background nohup process. 245. The method of any of the preceding embodiments such as embodiment 226, further comprising obtaining peptide ID data comprising at least one peptide ID determined by the plurality of micro-processes. 246. The method of any of the preceding embodiments such as embodiment 245, further comprising analyzing the peptide ID data to determine at least one identified protein. 247. The method of any of the preceding embodiments such as embodiment 226, wherein the plurality of micro-processes is executed by a plurality of micro-processors. 248. The method of any of the preceding embodiments such as embodiment 226, wherein the plurality of micro-processes is executed by a distributed network of computers. 249. The method of any of the preceding embodiments such as embodiment 226, wherein the mass spectra data comprises tandem mass spectra data. 250. The method of any of the preceding embodiments such as embodiment 226, wherein the plurality of mass spectra data comprises at least 1,000 mass spectra and is categorized in no more than 1 hour by the plurality of micro-processes. 251. The method of any of the preceding embodiments such as embodiment 226, wherein the plurality of mass spectra data comprises at least 5,000 mass spectra and is categorized in no more than 2 hour of total computational analysis by the plurality of micro-processes. 252. A computer system comprising at least one processor, a memory, and a software application executable by the at least one processor, said system configured to perform steps comprising: a) obtaining a plurality of mass spectra data; b) executing a plurality of micro-processes, said micro-processes comprising: i) selecting a first unanalyzed mass spectrum from the plurality of mass spectra data; ii) analyzing said first mass spectrum until a peptide ID is determined; and iii) categorizing said first mass spectrum; wherein a first micro-process and a second micro-process of the plurality of micro-processes operate concurrently. 253. The computer system of any of the preceding embodiments such as embodiment 252, wherein the selecting, analyzing, and categorizing the first mass spectrum is performed by the first micro-process. 254. The computer system of any of the preceding embodiments such as embodiment 252, wherein the selecting, analyzing, and categorizing a second mass spectrum is performed by the second micro-process. 255. The computer system of any of the preceding embodiments such as embodiment 252, wherein the plurality of micro-processes operates independently and concurrently. 256. The computer system of any of the preceding embodiments such as embodiment 252, wherein the plurality of micro-processes comprises selecting, analyzing, and categorizing mass spectra from the plurality of mass spectra data until said plurality of micro-processes is suspended or terminated. 257. The computer system of any of the preceding embodiments such as embodiment 252, wherein the plurality of micro-processes continues selecting, analyzing, and categorizing mass spectra until the plurality of mass spectra data has been categorized. 258. The computer system of any of the preceding embodiments such as embodiment 252, wherein the plurality of micro-processes comprises at least 10 micro-processes. 259. The computer system of any of the preceding embodiments such as embodiment 252, wherein each micro-process is run as a background nohup process. 260. The computer system of any of the preceding embodiments such as embodiment 252, wherein the plurality of mass spectra data comprises at least 3,000 mass spectra and is categorized in no more than 1 hour by the plurality of micro-processes. 261. The computer system of any of the preceding embodiments such as embodiment 252, wherein the plurality of mass spectra data comprises at least 6,000 mass spectra and is categorized in no more than 2 hour of total computational analysis by the plurality of micro-processes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The following illustrative examples are representative of embodiments of the systems, methods, and compositions described herein and are not meant to be limiting in any way.

Example 1—Mass Spectrometry Analysis Using Multiple Micro-Processes

A protein fraction purified from a biological sample is subjected to tryptic digestion and subsequent analysis by tandem mass spectrometry to generate raw tandem mass spectra. The raw tandem mass spectra are processed to extract tandem mass spectra data that is uploaded onto an SQL database deployed on a server. The tandem mass spectra data is stored on the SQL database as a 64-bot converted JSON representation of a 2-dimensional array containing all of the mass-charge (mz) and abundance values. In addition, an isotope reduced array is also stored on the SQL database, which includes the mono-isotopic mz, abundance, and charge state. A plurality of micro-processes is executed on a local computing system to analyze the tandem mass spectral data. The local computing system has a single-core processor that executes the plurality of micro-processes via multithreading. Each micro-process operates independently and in concurrently with the other micro-processes, selecting an unanalyzed mass spectrum from the mass spectra data stored on the SQL database, analyzing the mass spectrum to determine a peptide identification (ID), and then categorizing the mass spectrum as analyzed upon determining the peptide ID. Each micro-process then repeats the process and selects another unanalyzed mass spectrum from the mass spectra data. In this instance, the analysis includes searching a given mass spectrum against a library of known mass spectra stored on a MongoDB peptide sequence database run on the server. This process continues with each micro-process continuing to analyze mass spectra until all of the mass spectra data has been analyzed. The peptide IDs associated with the analyzed mass spectra are saved onto the SQL database. A subset of the mass spectra data does not successfully result in peptide IDs. However, a large majority of the data result in successful peptide identification. In addition, the entire mass spectra data set comprising 10,000 unique spectra and 100,000 total spectra is analyzed in less than 8 hours. The identified peptides are then downloaded from the SQL server and used for protein assembly and accounting. A peptide homology search is performed using a BLASTp script. Next, an R script is executed to perform observational frequency analysis and Fischer's p-value combination for protein false discovery rate (FDR) estimation. These analyses result in final peptide and spectral assignments to each identified protein. The final peptide and spectral assignment to a given protein is generated by expanding all spectra/peptide results by the total homology, and then collapsing back down to a single instance based on the final protein accounting or inclusion. The final protein accounting is also produced, which is a list of proteins ranked by p-value reported with the n number of peptide observations.

Example 2—Mass Spectrometry Analysis Using a Single Micro-Process

A protein fraction purified from a biological sample is subjected to tryptic digestion and subsequent analysis by tandem mass spectrometry to generate raw tandem mass spectra. The raw tandem mass spectra are processed to extract tandem mass spectra data. A single micro-process is executed on a local computing system to analyze the tandem mass spectral data. The micro-process selects an unanalyzed mass spectrum from the mass spectra data, analyzes the mass spectrum to determine a peptide identification (ID), and then categorizes the mass spectrum as analyzed upon determining the peptide ID. The micro-process then repeats the process and selects another unanalyzed mass spectrum from the mass spectra data. This micro-process continues to analyze mass spectra until all of the mass spectra data has been analyzed. On various occasions, the micro-process attempts analysis of a mass spectrum and is unable to successfully determine a peptide ID. The micro-process remains stuck on these occasions until it is terminated and restarted by the local computing system. Finally, the entire mass spectra data set comprising 10,000 unique spectra and 100,000 total spectra is analyzed after 24 hours. The identified peptides are then downloaded from the SQL server and used for protein assembly and accounting.

Example 3—Mass Spectrometry Analysis Using Multiple Micro-Process and Parallel Computing A protein fraction purified from a biological sample is subjected to tryptic digestion and subsequent analysis by tandem mass spectrometry to generate raw tandem mass spectra. The raw tandem mass spectra are processed to extract tandem mass spectra data that is uploaded onto an SQL database deployed on a server. A plurality of micro-processes is executed on a local computing system to analyze the tandem mass spectral data. The local computing system has a quad-core central processing unit (CPU). Each core processor executes a subset of the plurality of micro-processes. Each micro-process operates independently and in concurrently with the other micro-processes, selecting an unanalyzed mass spectrum from the mass spectra data stored on the SQL database, analyzing the mass spectrum to determine a peptide identification (ID), and then categorizing the mass spectrum as analyzed upon determining the peptide ID. The micro-process then repeats the process and selects another unanalyzed mass spectrum from the mass spectra data. In this instance, the analysis includes searching a given mass spectrum against a library of known mass spectra stored on a MongoDB peptide sequence database run on the server. This process continues with each micro-process continuing to analyze mass spectra until all of the mass spectra data has been analyzed. The peptide IDs associated with the analyzed mass spectra are saved onto the SQL database. A subset of the mass spectra data does not successfully result in peptide IDs. However, a large majority of the data result in successful peptide identification. In addition, the entire mass spectra data set comprising 10,000 unique spectra and 100,000 total spectra is analyzed in less than 4 hours. The remaining data analysis is performed as described in Example 1.

Example 4—Mass Spectrometry Analysis Using Multiple Micro-Process and Distributed Computing A protein fraction purified from a biological sample is subjected to tryptic digestion and subsequent analysis by tandem mass spectrometry to generate raw tandem mass spectra. The raw tandem mass spectra are processed to extract tandem mass spectra data that is uploaded onto an SQL database deployed on a server. A local computing system initiates the analysis by assigning the mass spectra data to a distributed network of computing systems for analysis. Each computing system in the network executes at least one micro-process. Each micro-process operates independently and in concurrently with the other micro-processes on a given computing system. Moreover, each computing system operates independently and concurrently with the other computing systems. The computing systems in the network are able to coordinate their analyses by referring to the SQL database that logs analyzed spectra and peptide IDs that are uploaded after analysis. The database can also have a status assigned to each mass spectrum that indicates whether the spectrum has not been selected for analysis, is currently be analyzed, has had a successful ID found, or has not yet had an ID found. This information can be used to prevent redundant analysis of an analyzed spectrum. Each micro-process selects an unanalyzed mass spectrum from the mass spectra data stored on the SQL database, analyzes the mass spectrum to determine a peptide identification (ID), and then categorizes the mass spectrum as analyzed upon determining the peptide ID. The micro-process then repeats the process and selects another unanalyzed mass spectrum from the mass spectra data. In the case that a mass spectrum fails to yield a peptide ID, the micro-process categorizes the mass spectrum as analyzed but without a peptide ID and continues onto the next mass spectrum. This process continues with each micro-process continuing to analyze mass spectra until all of the mass spectra data has been analyzed. The peptide IDs associated with the analyzed mass spectra are saved onto the SQL database. A subset of the mass spectra data does not successfully result in peptide IDs. However, a large majority of the data result in successful peptide identification. In addition, the entire mass spectra data set comprising 10,000 unique spectra and 100,000 total spectra is analyzed in less than 1 hour. The remaining data analysis is performed as described in Example 1.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method for analyzing mass spectra data, the method comprising:
    a) obtaining a biological sample;
    b) subjecting the biological sample to mass spectrometric analysis to generate a plurality of mass spectra data;
    c) executing a plurality of micro-processes, said micro-processes comprising:
        i) selecting a first unanalyzed mass spectrum from the plurality of mass spectra data;
        ii) analyzing said first mass spectrum until a peptide ID is determined; and
        iii) categorizing said first mass spectrum;
    wherein a first micro-process and a second micro-process of the plurality of micro-processes operate concurrently.

2. The method of claim 1, wherein selecting the first unanalyzed mass spectrum, analyzing the first mass spectrum, and the categorizing the first mass spectrum are performed by the first micro-process.

3. The method of claim 1, wherein the plurality of micro-processes further comprises:
    a) selecting a second unanalyzed mass spectrum from the plurality of mass spectra data;
    b) analyzing said second mass spectrum until a peptide ID is determined; and
    c) categorizing said second mass spectrum.

4. The method of claim 3, wherein selecting the second unanalyzed mass spectrum, analyzing the second mass spectrum, and categorizing the second mass spectrum is performed by the second micro-process.

5. The method of claim 3, wherein the plurality of micro-processes further comprises:
    a) selecting a third unanalyzed mass spectrum from the plurality of mass spectra data;
    b) analyzing said third mass spectrum until a peptide ID is determined; and
    c) categorizing said third mass spectrum.

6. The method of claim 5, wherein selecting the third unanalyzed mass spectrum, analyzing the third mass spectrum, and categorizing the third mass spectrum is carried out by a third micro-process.

7. The method of claim 6, wherein the first micro-process, the second micro-process, and the third micro-process operate independently.

8. The method of claim 1, wherein the first micro-process and the second micro-process operate independently.

9. The method of claim 1, wherein the plurality of micro-processes operates independently and concurrently.

10. The method of claim 1, wherein the plurality of micro-processes continues selecting, analyzing, and categorizing mass spectra until the plurality of mass spectra data has been categorized.

11. The method of claim 1, wherein analyzing comprises running a search of the first mass spectrum in a peptide sequence database, and wherein the search comprises searching the peptide sequence database for at least one candidate peptide with similar precursor mass.

12. The method of claim 11, wherein the search further comprises obtaining at least one theoretical spectrum for the at least one candidate peptide and scoring the at least one theoretical spectrum based on degree of matching with the first mass spectrum.

13. The method of claim 1, wherein the plurality of micro-processes comprises at least 10 micro-processes.

14. The method of claim 1, wherein the plurality of micro-processes is initiated by a series of nested calls.

15. The method of claim 1, wherein each micro-process is run as a background nohup process.

16. The method of claim 1, further comprising obtaining peptide ID data comprising at least one peptide ID determined by the plurality of micro-processes.

17. The method of claim 1, wherein the plurality of micro-processes is executed by a plurality of micro-processors or by a distributed network of computers.

18. The method of claim 1, wherein the plurality of mass spectra data comprises tandem mass spectra data.

19. The method of claim 1, wherein the plurality of mass spectra data comprises at least 1,000 mass spectra and is categorized in no more than 1 hour by the plurality of micro-processes.

20. The method of claim 1, wherein the plurality of mass spectra data comprises at least 5,000 mass spectra and is categorized in no more than 2 hour of total computational analysis by the plurality of micro-processes.

* * * * *